(12) United States Patent
Bendory et al.

(10) Patent No.: US 11,510,564 B2
(45) Date of Patent: Nov. 29, 2022

(54) SEEKER WITH DILATOR

(71) Applicant: 3NT MEDICAL LTD., Rosh Haayin (IL)

(72) Inventors: Ehud Bendory, Herzliya (IL); Eran Bendory, Maccabin-re 'ut (IL); Gil Hefer, Shimshit (IL)

(73) Assignee: 3NT Medical Ltd., Rosh Ha'ayin (IL)

( * ) Notice: Subject to any disclaimer, the term of this patent is extended or adjusted under 35 U.S.C. 154(b) by 819 days.

(21) Appl. No.: 16/334,428

(22) PCT Filed: Sep. 20, 2017

(86) PCT No.: PCT/IB2017/001321
§ 371 (c)(1),
(2) Date: Mar. 19, 2019

(87) PCT Pub. No.: WO2018/055450
PCT Pub. Date: Mar. 29, 2018

(65) Prior Publication Data
US 2020/0288962 A1   Sep. 17, 2020

Related U.S. Application Data

(60) Provisional application No. 62/430,027, filed on Dec. 5, 2016, provisional application No. 62/397,714, filed on Sep. 21, 2016.

(51) Int. Cl.
*A61B 1/32* (2006.01)
*A61B 1/233* (2006.01)
(Continued)

(52) U.S. Cl.
CPC ............ *A61B 1/32* (2013.01); *A61B 1/00082* (2013.01); *A61B 1/00147* (2013.01); *A61B 1/01* (2013.01);
(Continued)

(58) Field of Classification Search
CPC ... A61B 1/32; A61B 1/00082; A61B 1/00147; A61B 1/01; A61B 1/018; A61B 1/227;
(Continued)

(56) References Cited

U.S. PATENT DOCUMENTS 4,299,226 A * 11/1981 Banka ................. A61M 25/104
                                                600/434
6,048,358 A *  4/2000 Barak ................ A61B 17/0057
                                                606/213
(Continued)

FOREIGN PATENT DOCUMENTS

WO      WO2011140535      11/2011

OTHER PUBLICATIONS

Invitation to Pay Additional Fees for PCT/IB2017/001321, dated Feb. 12, 2018, 15 pages.
(Continued)

*Primary Examiner* — Anh Tuan T Nguyen
*Assistant Examiner* — Shankar Raj Ghimire
(74) *Attorney, Agent, or Firm* — Merchant & Gould P.C.

(57) ABSTRACT

A seeker device for facilitating access to a desired location within an ear, nose, throat or other location in a body may include a proximal shaft, an elastic distal portion, and an atraumatic distal tip. The elastic distal portion has a default shape with at least one curve to facilitate advancement of a distal end of the elastic distal portion through various anatomical passageways, toward the desired location. In some embodiments, the seeker device may be paired with a dilator device, to perform a dilation procedure on an anatomical structure in the ear, nose, throat or other part of the body. In other embodiments, the seeker device may be paired with a flexible endoscope, to facilitate visualization of an anatomical structure or area.

17 Claims, 38 Drawing Sheets

(51) Int. Cl.
  *A61B 1/00* (2006.01)
  *A61B 1/01* (2006.01)
  *A61B 1/018* (2006.01)
  *A61B 1/227* (2006.01)
  *A61B 17/00* (2006.01)
  *A61B 17/24* (2006.01)
  *A61B 17/34* (2006.01)

(52) U.S. Cl.
  CPC .............. *A61B 1/018* (2013.01); *A61B 1/227* (2013.01); *A61B 1/233* (2013.01); *A61B 17/00234* (2013.01); *A61B 17/24* (2013.01); *A61B 17/3417* (2013.01); *A61B 2017/00296* (2013.01); *A61B 2017/00331* (2013.01); *A61B 2017/00557* (2013.01); *A61B 2017/00867* (2013.01)

(58) Field of Classification Search
  CPC .............. A61B 1/233; A61B 17/00234; A61B 17/3417; A61B 2017/00557
  See application file for complete search history.

(56) References Cited

U.S. PATENT DOCUMENTS

| | | | |
|---|---|---|---|
| 7,172,562 B2 * | 2/2007 | McKinley | A61B 5/103 33/511 |
| 7,381,205 B2 * | 6/2008 | Thommen | A61M 25/0147 604/523 |
| 7,717,933 B2 | 5/2010 | Becker | |
| 7,740,642 B2 | 6/2010 | Becker | |
| 7,753,929 B2 | 7/2010 | Becker | |
| 8,080,000 B2 * | 12/2011 | Makower | A61B 1/267 604/510 |
| 8,090,433 B2 | 1/2012 | Makower et al. | |
| 8,100,933 B2 | 1/2012 | Becker | |
| 8,317,816 B2 | 11/2012 | Becker | |
| 8,764,709 B2 | 7/2014 | Chang et al. | |
| 8,764,786 B2 | 7/2014 | Becker | |
| 8,777,926 B2 | 7/2014 | Chang et al. | |
| 8,961,398 B2 | 2/2015 | Makower et al. | |
| 8,979,888 B2 * | 3/2015 | Morriss | A61B 1/233 606/196 |
| 9,238,125 B2 | 1/2016 | Vaccaro et al. | |
| 9,457,175 B2 | 10/2016 | Becker | |
| 2003/0114878 A1 * | 6/2003 | Diederich | A61M 25/10 606/192 |
| 2007/0129751 A1 * | 6/2007 | Muni | A61M 31/005 606/196 |
| 2008/0097154 A1 * | 4/2008 | Makower | A61B 1/267 600/114 |
| 2008/0172033 A1 * | 7/2008 | Keith | A61B 1/018 604/506 |
| 2010/0030113 A1 * | 2/2010 | Morriss | A61M 29/00 600/585 |
| 2010/0099946 A1 * | 4/2010 | Jenkins | A61B 17/24 600/104 |
| 2010/0130996 A1 * | 5/2010 | Doud | A61M 5/34 606/159 |
| 2010/0274188 A1 * | 10/2010 | Chang | A61B 1/227 604/96.01 |
| 2012/0071857 A1 * | 3/2012 | Goldfarb | A61M 25/09041 604/514 |
| 2012/0109079 A1 * | 5/2012 | Asleson | A61F 2/2427 604/272 |
| 2013/0066358 A1 | 3/2013 | Nalluri | |
| 2013/0096378 A1 * | 4/2013 | Alexander | A61B 1/0014 600/106 |
| 2013/0261388 A1 | 10/2013 | Jenkins | |
| 2014/0243872 A1 | 8/2014 | Cordray | |
| 2015/0133737 A1 * | 5/2015 | Bacich | A61B 1/303 600/204 |
| 2015/0202089 A1 * | 7/2015 | Campbell | A61B 1/233 600/478 |
| 2015/0289754 A1 | 10/2015 | Bendory | |
| 2016/0074639 A1 * | 3/2016 | Li | A61M 29/02 606/196 |
| 2016/0287065 A1 * | 10/2016 | Ha | A61B 1/00133 |

OTHER PUBLICATIONS

International Search Report and Written Opinion for PCT/IB2017/001321, dated Apr. 9, 2018, 18 pages.

* cited by examiner

SEEKER WITH DILATOR

CROSS-REFERENCE TO RELATED APPLICATIONS

This application is a National Stage Application of PCT/IB2017/001321, filed Sep. 20, 2017, which claims the benefit of priority to U.S. Provisional Patent Application No. 62/397,714, filed Sep. 21, 2016, and 62/430,027, filed Dec. 5, 2016, both entitled "Seeker With Dilator." The entireties of all of the above applications are herein incorporated by reference for all purposes.

TECHNICAL FIELD

This application is generally directed to medical and surgical devices, systems and methods for use in otolaryngology. More specifically, the application is directed to medical and surgical devices, systems and methods for facilitating access, dilation and/or visualization of various anatomical structures in the ear, nose and throat.

BACKGROUND

Sinusitis is a condition affecting over 35 million Americans and similarly large populations in the rest of the developed world. Sinusitis occurs when one or more of the four paired sinus cavities (maxillary, ethmoid, frontal and/or sphenoid sinuses) become inflamed, thus causing obstruction or otherwise compromising sinus drainage. Sinusitis, and especially chronic or recurring sinusitis, can be extremely debilitating, with patients suffering from headache, facial pain, toothache, inner ear problems, and other symptoms of head and neck discomfort. Thus, sinusitis is a significant and serious health problem that affects many millions of patients worldwide.

Normally, the paranasal sinus cavities produce mucus, which is then moved, by beating cilia, out of the sinus cavities and into nasal cavity and down the throat. Altogether, the sinuses produce approximately one liter of mucus daily, so the effective transport of this mucus is important to sinus health. Each sinus cavity has a drainage pathway or outflow tract opening into the nasal cavity. This drainage passageway can include an ostium, as well as a "transition space" in the region of the ostium, such as the "frontal recess," in the case of the frontal sinus, or the "ethmoid infundibulum," in the case of the maxillary sinus. When the mucosa (or "lining") of one or more of the ostia or regions near the ostia become inflamed, the egress of mucus is interrupted, thus setting the stage for an infection and/or inflammation of the sinus cavity, i.e., sinusitis.

Although some cases of sinusitis may be treatable with appropriate medications, such as antihistamines or antibiotics, in some cases sinusitis persists for months or more, a condition called chronic sinusitis. Other patients suffer from multiple episodes of sinusitis in a given period of time, a condition called recurrent sinusitis. Many chronic and recurrent sinusitis patients do not respond to medical therapy and thus may seek surgical options.

Functional endoscopic sinus surgery (FESS) is currently the most common type of surgery used to treat chronic sinusitis. In a typical FESS procedure, an endoscope is inserted into the nostril along with one or more surgical instruments. The surgical instruments are then used to cut out mucosal tissue and/or bone, to surgically enlarge one or more sinus ostia and often remove other growths and structures in the nasal cavity, in an attempt improve drainage from the sinuses. Although FESS procedures work well for many patients, the significant removal of tissue results in a very invasive surgical procedure, which typically results in a lengthy recovery period, with significant post-operative pain, discomfort and bleeding, which requires painful packing, removal and repacking of the nasal cavity with gauze. This packing process, as well as the general pain and other post-operative complications, often require a FESS patient to return to the physician's office multiple times after surgery.

More recently, a less invasive, intranasal sinus surgery procedure, known as balloon sinus dilation or balloon sinuplasty, has been developed. Balloon sinuplasty involves advancing a small, flexible balloon catheter into the effected sinus ostium and inflating the balloon to dilate the ostium. The balloon is noncompliant, so that when it inflates it is strong enough to break the very thin bone that forms the sinus ostium. Thus, when the ostium heals, it heals in the dilated configuration, which ideally restores normal drainage of mucus from that sinus. Typically, balloon sinuplasty is performed without removing any tissue from the paranasal sinuses or nasal cavity, and the patient often has very few or no post-operative symptoms or complaints.

When performing balloon sinus dilation, the surgeon inserts a sinus guide catheter or cannula through the nostril, to gain access to the affected sinus ostium, under endoscopic visualization. A guidewire, with or without an illumination system, is then introduced into the targeted paranasal sinus via the sinus guide catheter, and the guide catheter is removed. Once access to the intended targeted location is confirmed by light or fluoroscopy, a flexible catheter, carrying a balloon, is introduced into the sinus cavity over the sinus guidewire, locating the balloon in the blocked ostium. The illumination system, if used, provides transcutaneous (through the skin) light transmission that the surgeon relies on when estimating desired balloon placement. Once the desired balloon position has been visually confirmed, the balloon is gradually inflated to dilate the narrowed or blocked ostium. The balloon is then deflated and removed. Next, an irrigation catheter may be advanced over the guidewire to flush out mucus. Finally, the sinus irrigation catheter is removed from the sinus, to allow the sinus cavity to drain.

While highly promising, existing balloon sinuplasty systems and methods have several drawbacks. One significant drawback is that it can often be very challenging to visualize a paranasal sinus ostium using a conventional endoscope and to access the ostium using available balloon dilation tools. The anatomy of the nasal cavity is one of very tight spaces filled with many protruding structures made of bone covered with mucous membrane. It is often quite challenging, for example, to advance a guide catheter through this tight nasal cavity anatomy to arrive at a sinus ostium, especially without causing damage and post-operative pain to the patient. Some of the ostia of the paranasal sinuses, such as those of the maxillary sinuses, are located at relatively sharp angles, relative to the nasal cavity. This makes accessing those ostia even more challenging. For the same reasons, it is often quite challenging to visualize a sinus ostium using an endoscope. Although angled endoscopes are available, they require multiple different endoscopes to view different sinuses. Adjustable-angle endoscopes tend to be difficult to use and often provide lower quality imaging than fixed-angle endoscopes.

Another shortcoming of available sinus dilation techniques is that they require multiple steps, multiple instruments and multiple people to perform a procedure. For example, it can be very challenging for one physician to advance a guide catheter to a desired location in the nasal cavity, advance the guidewire through the guide catheter, remove the guide catheter, advance the balloon catheter over the guidewire to the correct location in the ostium, and visualize the sinus using an illumination system. Even if one physician performs all of these steps, currently available balloon catheter inflation devices typically require that a second person hold the balloon inflation device and perform the inflation, while the physician manipulates (or holds steady) the balloon catheter system. Additionally, ear, nose and throat surgeons (also called "otolaryngologists") are typically trained to use short, rigid surgical tools developed specifically for otolaryngology procedures—they are typically not trained in catheter-based procedures like balloon dilation.

In short, the technical challenges and relative complexity of balloon sinuplasty, as well as the need for at least two care providers to perform the procedure, are not ideal. These challenges have led to balloon sinuplasty being most commonly performed in operating rooms, rather than in a more comfortable and less expensive physician's office. The complexity of currently available balloon sinuplasty systems also adds expense, due to the large number of system components.

Balloon dilation has also been mentioned as a possible treatment option for other ear, nose and throat ailments, such as Eustachian tube malfunction and airway constrictions. These treatments have similar challenges to those of balloon sinuplasty.

Therefore, it would be desirable to have improved devices, systems and methods for accessing, dilating and/or visualizing structures in the ear, nose and throat, such as paranasal sinuses and Eustachian tubes. Ideally, such devices, systems and methods would be simpler to use and less expensive than existing systems. It would also be ideal if one physician could access, dilate and/or visualize a paranasal sinus, without requiring help from a second physician or assistant. Ideally, many or all of the techniques used to access, visualize and/or dilate an ear, nose or throat structure might be performed by one physician using just one hand. At least some of these objectives will be addressed by the embodiments described in this application.

BRIEF SUMMARY

This application describes a new and improved seeker device (or simply a "seeker"), which facilitates accessing anatomical locations within the ear, nose, throat or other parts of the body. The seeker device includes an elastic distal portion with a default shape that includes at least one curve or bend, and often two more curves or bends. (For the purposes of this application, the term "curve" includes bends, kinks, turns, angles, or the like.) Each seeker device may include an elastic distal portion with a shape specifically designed to access one specific anatomical area or structure. Such anatomical areas or structures include, but are not limited to a left or right maxillary sinus, frontal sinus, sphenoid sinus, ethmoid sinus, or Eustachian tube, a stricture in an area of the upper airway, such as the trachea, a portion of an esophagus, a bile duct, or a ureter. Unlike typical rigid or malleable seekers, the seeker devices described in this application are able to change, within the body, from a first constrained configuration for passage through tight, small-diameter anatomical passageways or similar anatomy, to a second, default configuration that includes one or more curves specifically designed to facilitate accessing the desired anatomical structure or location. In some cases, in fact, the elastic distal portion may "spring" or "jump" into or through the target anatomical location when it changes from its constrained configuration to its default configuration. This change of shape within the body is unique to the seeker devices described herein.

In its simplest form, the seeker described in this application may be used by itself or with an optional sheath, to facilitate access to a desired anatomical location in the body. In some embodiments, however, the seeker may be paired with a dilator device, such as a balloon dilator, for dilating a structure in the body. In general, such dilators include a flexible distal portion, which rests over the elastic distal portion of the seeker and is sufficiently flexible to at least partially assume the default shape of the seeker when it is released from constraint. The seeker thus facilitates access to the structure of interest and also positions the dilator at the target structure for performing a dilation procedure. Unlike currently available balloon dilator devices, the seeker/dilators described in this application do not require any advancing or retracting of the dilator over the seeker during the procedure, thus making each procedure significantly simpler and easier for one physician to perform, and also reducing the chance for user error and damage to the dilator.

In other embodiments, the seeker may be paired with a flexible endoscope. As with the dilator, at least part of the endoscope is sufficiently flexible to assume the default shape of the seeker's elastic distal portion. The seeker may thus be used in this seeker/endoscope pair to help access an anatomical location to be visualized with the endoscope.

In one aspect of the present application, a system for dilating a structure in an ear, nose or throat of a patient may include a seeker device, a dilator device, a handle and an inflation device. The seeker device may include a proximal shaft and an elastic distal portion that has a default shape with at least one curve configured to facilitate advancement of a distal end of the elastic distal portion into a desired location within the ear, nose or throat. The dilator device may include a proximal portion and a flexible distal portion, including a dilation member configured for placement over the elastic distal portion of the seeker device. The dilation member includes a first lumen for receiving the seeker device and a second lumen for receiving an inflation substance. The flexible distal portion is sufficiently flexible to at least partially assume the default shape of the elastic distal portion of the seeker device when the flexible distal portion is located over the elastic distal portion. The handle is configured to attach to the proximal shaft of the seeker device and the proximal portion of the dilator device. The inflation device is removably attachable to the handle and the dilator device and is configured to allow a user to hold the handle with one hand and advance the inflation substance out of the inflation device to inflate the dilation member with the same hand.

In some embodiments, the proximal shaft and the elastic distal portion of the seeker device may be made of one type of material, such as stainless steel or another metal. In other embodiments, the proximal shaft may be made of a first material, and the elastic distal portion may be made of a second material. The first material may be any suitable material, such as but not limited to Nitinol, stainless steel, titanium, other metals, PEEK and other polymers. The second material may be also be any suitable material, such as but not limited to stainless steel or other metal, or an elastic, super-elastic or shape-memory material, such as but not limited to Nitinol, a copper-aluminum-nickel alloy, a shape-memory polymer, spring stainless steel, an elastic polymer, other shape-memory materials and other superelastic materials. Typically, though not necessarily, the proximal shaft is significantly longer than the elastic portion. The seeker device may also include an atraumatic distal tip, such as a ball-shaped tip, on its distal end. In some embodiments, the elastic distal portion of the seeker device includes a first curve in a first plane and a second curve in a second plane. Other embodiments may include first and second curves in the same plane, more than two curves in the same plane, more than two curves in multiple planes, etc.

The dilation member of the dilator device may be any suitable dilator. In one embodiment it is an inflatable, non-compliant balloon. In some embodiments, the proximal portion of the dilator device comprises a rigid shaft fixedly attached to the handle, and the proximal shaft of the seeker device is configured to pass through the first lumen of the dilator device and into the handle. The handle, in turn, may include a locking mechanism for removably locking the proximal shaft of the seeker device to the handle. In some embodiments, the first lumen of the dilator device is located coaxially within the second lumen. Alternatively, the first lumen of the dilator device may be located beside the second lumen. In some embodiments, the first lumen of the dilator device may have a first opening at its distal end and a second opening in a side of the dilator device located proximal to the dilation member. In other words, this type of embodiment may include a "rapid exchange" type of lumen configuration for passing the dilator device over the seeker. Generally, although not necessarily, the second opening is located closer to a proximal end of the dilation member than to a proximal end of the dilator device.

As mentioned above, the handle may include a locking member configured to removably lock the proximal shaft of the seeker device to the handle, to prohibit the proximal shaft from moving relative to the handle or the dilator device. The proximal portion of the dilator device may permanently and fixedly attached to the handle or alternatively may be removably attached to the handle. Thus, after the seeker is locked to the handle and during use of the system, the seeker and the dilator are fixed, relative to one another and to the handle, so the dilator does not need to (and in fact does not) advance or retract over the seeker during the procedure. In some embodiments, the handle may further include a housing for accepting and housing at least a portion of the inflation device. In some embodiments, the inflation device may be a syringe, and the housing is thus configured to house a distal portion of the syringe, such that when the syringe is coupled with the handle, the plunger acts as a trigger for inflating the dilation member.

In some embodiments, the inflation device may further include a pressure release valve to prevent over-inflation of the dilation member. In some embodiments, the inflation device may further include a spring coupled with the plunger to cause the dilation member to automatically deflate if the plunger is not depressed by a user. The system may also include a tube configured to connect a distal end of the syringe to the dilator device.

The system may also optionally include a sheath for placement over at least the elastic distal portion of the seeker device and the dilation member of the dilator device. The sheath is sufficiently rigid to hold the elastic distal portion in a relatively straight, constrained configuration for delivery through anatomy of the patient toward the desired location. Typically, the sheath is slidable from an advanced position, in which the sheath covers the elastic distal portion and the dilation member and thus maintains the elastic distal portion and the dilation member in the constrained configuration, to a retracted position, in which the sheath does not cover the elastic distal portion or the dilation member.

In some embodiments, the system includes multiple alternative seeker devices, each with a different shape specifically designed to access a particular anatomical structure or location. As such, the curve (or curves) of the elastic distal portion of each of the alternative seeker devices has a specific default shape. The target locations for the seeker devices include, but are not limited to, a left maxillary sinus, a right maxillary sinus, a left frontal sinus, a right frontal sinus, a left sphenoid sinus, a right sphenoid sinus and a Eustachian tube.

In another aspect of the present application, a system for visualizing a structure in an ear, nose or throat of a patient may include a seeker and handle as described above and a flexible endoscope. The endoscope includes at least one lumen for allowing the endoscope to pass over the seeker device. Furthermore, at least part the endoscope is sufficiently flexible to at least partially assume the default shape of the elastic distal portion of the seeker device when the at least part of the endoscope is located over the elastic distal portion.

In another aspect of this application, a seeker device is described for facilitating access to a desired location within an ear, nose or throat of a patient. The seeker, as mentioned above, may include a proximal shaft, an elastic distal portion having a default shape with at least one curve configured to facilitate advancement of a distal end of the elastic distal portion through the ear, nose or throat of the patient, toward the desired location, and an atraumatic tip at the distal end of the elastic distal portion.

The "rigid" proximal shaft, in some embodiments, is rigid only in relation to the elastic distal portion. In many embodiments, the proximal shaft portion has a level of stiffness sufficient to facilitate advancement of the seeker through tight anatomy. The proximal shaft portion in these embodiments provides the seeker with "pushability" or "torqueability." Thus, in some embodiments, such as when the seeker is used by itself or with a sheath to gain access to anatomy, the proximal shaft portion might be quite rigid, for example a solid or hollow rigid shaft made of stainless steel or other metal. In other embodiments, however, the proximal shaft portion may be quite thin and not very rigid. For example, in embodiments where the seeker is paired with a dilator device, the dilator device may include a rigid shaft, and the seeker may be passed through the rigid shaft of the dilator and attached to a handle. The dilator shaft, in such embodiments, provides the desired pushability and torqueability, and the seeker proximal shaft might be relatively thin, to fit through a lumen of the dilator. In one embodiment, for example, the entire seeker device may be fabricated as one, continuous piece of Nitinol. The proximal portion may be slightly wider in diameter than the elastic distal portion, or the two portions may have the same diameter. A distal, ball-shaped tip may also be formed from the same piece of Nitinol in some embodiments.

In some embodiments, the device may also include a sheath for placement over the elastic distal portion during advancement through the ear, nose or throat. The sheath is sufficiently rigid to maintain the elastic distal portion in a relatively straight, constrained configuration until the elastic distal portion is released from the sheath. In all other respects, the seeker device may be as described above or further below.

In another aspect of the present disclosure, a method for accessing a desired location within an ear, nose or throat of a patient may first involve advancing an elastic distal portion of a seeker device through the ear, nose or throat of the patient in a constrained configuration. Typically, the elastic distal portion has an atraumatic distal tip at one end and a proximal shaft at an opposite end. The method may next involve causing the elastic distal portion to change from the constrained configuration to a default configuration having at least one curve. Finally, the method may involve advancing at least the atraumatic distal tip of the elastic distal portion to the desired location within the ear, nose or throat.

Optionally, the method may also involve selecting the seeker device from a collection of multiple seeker devices, where the curve(s) of the elastic distal portion of each of the seeker devices has a specific default shape configured to facilitate access to one specific desired location. Again, the specific desired location may include, but is not limited to, a left maxillary sinus, a right maxillary sinus, a left frontal sinus, a right frontal sinus, a left sphenoid sinus, a right sphenoid sinus and a Eustachian tube. In alternative embodiments, any other location in the ear, nose, throat or other part of the body may be accessed. As mentioned above, in some embodiments, the elastic distal portion may be constrained within a sheath while the distal elastic portion is advanced through the ear, nose or throat. In such embodiments, causing the elastic distal portion to change from the constrained configuration to the default configuration involves retracting the sheath proximally over the seeker device and/or advancing the elastic portion out of the sheath. In other embodiments, where a sheath is not used, causing the elastic distal portion to change from the constrained configuration to the default configuration may simply involve advancing the elastic distal portion beyond a constraining anatomical structure in the ear, nose or throat.

In some embodiments, advancing the atraumatic distal tip of the elastic distal portion to the desired location within the ear, nose or throat occurs automatically, when the elastic distal portion changes from the constrained configuration to the default configuration. For example, the desired location may be a paranasal sinus, and the atraumatic distal tip may springs (or "jump") through an ostium of the paranasal sinus when the distal portion changes from the constrained configuration to the default configuration. In embodiments where the desired location is a paranasal sinus, the method may optionally further involve dilating an ostium of the paranasal sinus using an expandable dilation member disposed over the elastic distal portion of the seeker device, without advancing or retracting the expandable dilation member along the seeker device before dilating.

In another aspect of the present application, a method for dilating a structure in an ear, nose or throat of a patient may first involve advancing an elastic distal portion of a seeker device, with an expandable dilation member disposed over it, through the ear, nose or throat of the patient in a constrained configuration, where the elastic distal portion has an atraumatic distal tip at one end. The method may next involve causing the elastic distal portion to change from the constrained configuration to a default configuration having at least one curve. The expandable dilation member is sufficiently flexible to at least partially assume the default shape of the elastic distal portion of the seeker device. Next, the method involves advancing at least the atraumatic distal tip of the elastic distal portion to a desired location within the ear, nose or throat. Finally, the method involves expanding the dilation member, without advancing or retracting the expandable dilation member along the seeker device, to dilate the ostium of the paranasal sinus.

The method may include any of the additional steps and/or details described above. The structure to be dilated may be, in some embodiments, a paranasal sinus ostium or a Eustachian tube. In some embodiments, the dilation member may be an inflatable, non-compliant balloon, and expanding the dilation member thus involves inflating the balloon with a fluid. For example, inflating the balloon may involve activating an inflation device coupled with a handle, and the seeker device and a dilator device of which the dilation member is a part may both be attached to the handle. In such an embodiment, the method may also involve, before advancing the elastic distal portion through the ear, nose or throat: passing the seeker device through a first lumen of the dilator device, where a second lumen of the dilator device comprises an inflation lumen; locking the seeker device to the handle, to prevent the seeker device from moving relative to the handle or the dilator device; and attaching the inflation device to the dilator device. In some embodiments, the method may also optionally include, before passing the seeker device through the dilator device, attaching the dilator device fixedly to the handle, so that once the seeker device is locked to the handle, the dilator device and the seeker device cannot move relative to the handle. In alternative embodiments, the dilator device is already provided permanently fixed to the handle. The method may also include attaching the inflation device to the handle. In some embodiments, the inflation device may be a syringe, and activating the inflation device may involve depressing a plunger of the syringe.

In some embodiments, all of the steps of the method are performed with one hand of a user. Alternatively, some of the steps are performed with one hand, such as steps of advancing, inflating, etc., and one or more steps may typically be performed using two hands, such as attaching the inflation device to the handle. Any of the method embodiments may also include visualizing the structure in the ear, nose or throat, using an endoscope.

In another aspect of the present disclosure, a method for visualizing a structure in an ear, nose or throat of a patient may involve advancing an elastic distal portion of a seeker device through the ear, nose or throat of the patient in a constrained configuration, where the elastic distal portion has an atraumatic distal tip at one end and a proximal shaft at an opposite end. As described above, the method may next involve causing the elastic distal portion to change from the constrained configuration to a default configuration having at least one curve and advancing at least the atraumatic distal tip of the elastic distal portion to a desired location within the ear, nose or throat. The visualization method may then involve advancing a flexible endoscope over the elastic distal portion of the seeker device toward the structure in the ear, nose or throat, where at least part of the flexible endoscope is sufficiently flexible to at least partially assume the default shape of the elastic distal portion of the seeker device. After the endoscope is advanced, the method includes visualizing the structure in an ear, nose or throat with the flexible endoscope. In at least some embodiments, the method for visualizing thus differs from the method for dilating, in that the flexible endoscope is typically, though not necessarily, advanced over the seeker, whereas the dilator remains stationary relative to the seeker. In all other respects, the method may include any of the additional optional steps or details described above.

These and other aspects and embodiments of the present application are described in further detail below, in relation to the attached drawing figures.

DETAILED DESCRIPTION

Figure 1A:
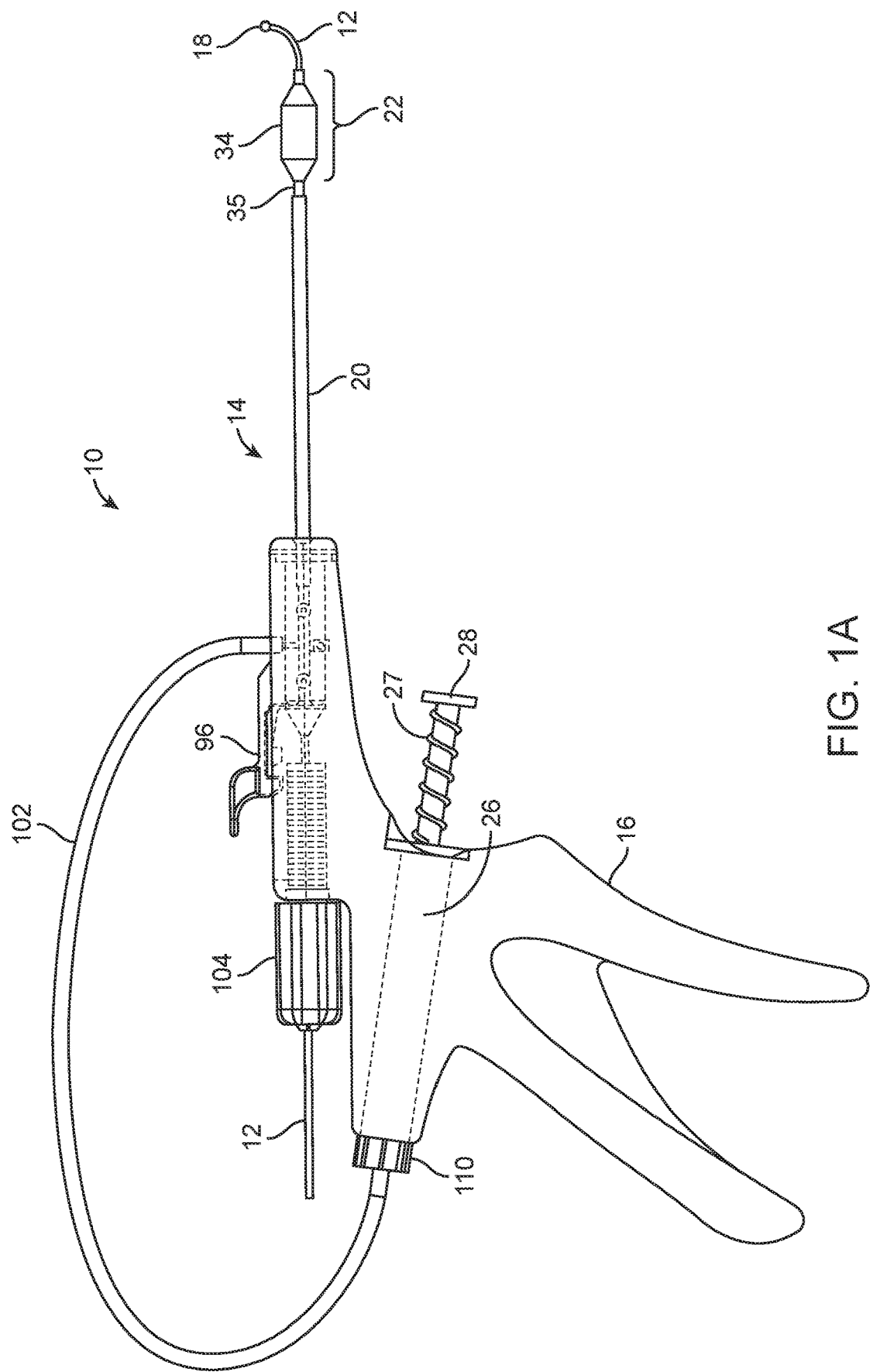
FIG. 1A is a side view of a dilation system for dilating an anatomical structure in a body, according to one embodiment.

The embodiments described below are directed to devices, systems and methods for accessing, visualizing and/or dilating any suitable ear, nose or throat structure. For ease of description, ear, nose and throat structures may be referred to herein as "ENT structures" or "an ENT structure." Such structures may include, but are not limited to, an ostium or area near an ostium of any paranasal sinus (maxillary, frontal, sphenoid or ethmoid), a Eustachian tube or a constricted trachea or throat. In alternative embodiments, the devices, systems and methods may instead be used to access, visualize and/or dilate an anatomical structure outside of the ear, nose or throat. For example, in one embodiment, the method and system described herein might be used to dilate an esophagus at its juncture with the stomach. In other embodiments, the method and system may be used to dilate a ureter, another portion of the urinary tract or a bile duct, for example to facilitate removal of a renal stone or gall stone. Therefore, although this Detailed Description focuses on embodiments for treatment of ENT structures, this should not be interpreted as limiting the scope of the invention, which may be applied to any other suitable structure in a human or animal body.

The various embodiments described herein all include a seeker device. The seeker, which may also be referred to as a "finder," "probe," "stylet" or any other similar name, includes a proximal shaft portion and an elastic distal portion. In some embodiments, the proximal shaft may be stiffer (or "more rigid") than the elastic distal portion. In some embodiments, this extra rigidity in the proximal shaft provides the seeker with sufficient "pushability" and/or "torqueability," to allow a user to advance the seeker through a nasal cavity or other ENT anatomy, to a structure of interest. The distal portion of the seeker, which typically but not necessarily includes an atraumatic distal tip, is designed to assume a first, constrained configuration to facilitate advancement of the seeker through anatomy and to change to a default, curved configuration when released from constraint. Each seeker may have a specific configuration designed to help the user access a specific anatomy, such as one of the paranasal sinuses or a Eustachian tube. The elastic distal portion in the constrained configuration may be relatively straight in some embodiments and may be curved in other embodiments. In embodiments where the constrained configuration includes a curve, the curve may be in a first plane, and the default configuration of the elastic distal portion may include a second curve in a second plane. The elastic distal portion in the default, curved configuration typically includes at least one curve and may include multiple curves in one or more planes, to help facilitate accessing an anatomical structure. Compared to previously described seekers, the seekers described herein allow for enhanced maneuverability. The elastic nature and curved shape of the distal portion, unlike rigid or malleable seekers described in the past, allows the distal portion to spring from a constrained configuration to a curved, default configuration, the latter of which is specifically designed to facilitate access to a given anatomy. A physician using the seeker can thus advance the seeker posteriorly, by holding the proximal portion of the seeker, and have the elastic distal portion of the seeker automatically move sideways (or sometimes even "jump"), into an opening to the side of the anatomy through which the seeker is being advanced. For example, the user may advance the seeker in a posterior direction through the nasopharynx and have the distal portion jump into the Eustachian tube. In various alternative embodiments, the seeker may be combined with a dilator device or a visualization device, either of which may be guided by the seeker to a desired location in the ear, nose, throat or other part of the body.

Referring now to FIGS. 1A-1I, one embodiment of a balloon dilation system 10 (or "seeker/dilator system") will be described. As illustrated in FIG. 1A, dilation system 10 may include a seeker 12 (or "seeker device"), a dilator 14 (or "dilator device") and a handle 16. In some embodiments, system 10 may also include an inflation device 26, but in alternative embodiments inflation device 26 may be available separately from system 10. Seeker 12 may include an atraumatic distal tip 18, such as a ball-shaped tip, which is visible outside of dilator device 14 in FIG. 1A, while a proximal end of seeker 12 extends out of a proximal end of handle 16. Dilator device 14 may include a proximal shaft 20, with a connector hub 96 attached at one end and a flexible distal portion 22 at an opposite end. Connector hub 96 may be used for connecting dilator device 14 to handle 16 and for connecting an inflation tube 102 to an inflation lumen of dilator device 14. Flexible distal portion 22 is generally sufficiently flexible to conform to the default shape of the elastic distal portion of seeker 12, which resides in an inner lumen of dilator device 14. Flexible distal portion 14 generally includes a flexible distal shaft 35 and a balloon dilator 34.

In some embodiments, inflation device 26, such as but not limited to a syringe, may be attached to handle 16, such as by inserting into a chamber or housing of handle 16, and may include a plunger 28 or alternatively a trigger or other activation mechanism. In the embodiment shown, plunger 28 is wrapped with a spring 27, so that inflation device 26 is spring loaded and automatically deflates balloon dilator 34 if the user releases pressure from plunger 28. Handle 16 may have a generally ergonomic design, for fitting comfortably in a user's hand. Handle 16 may be fixedly attached to the proximal end of shaft 20, either removably, as in the illustrated embodiment, or permanently in alternative embodiments. Seeker 12 may extend through an inner lumen of dilator device 14, through handle 16, and out the proximal end of handle 16. Handle 16 may also include a seeker locking mechanism 104, for locking seeker 12 to handle 16. In this embodiment, therefore, when system 10 is ready to use, both seeker 12 and dilator device 14 are attached to handle 16 in a fixed manner, so they cannot move relative to handle 16 or to each other. For illustrative purposes, an elastic distal portion 32 (FIG. 1B) of seeker 12 is shown outside of the distal end of dilator device 14. In use, seeker 12 would typically be advanced more proximally through the inner lumen of dilator device 14 before insertion of system 10 into a patient so that only atraumatic tip 18 would protrude out of the distal end of dilator device 14. When elastic distal portion 32 of seeker 12 is located inside flexible distal portion 22 of dilator device 14, flexible distal portion 22 will at least partially assume the default, curved shape of elastic distal portion 32. This will be described and illustrated further below.

Using this embodiment of system 10, a user may hold handle 16 and advance the distal portions of seeker 12 and dilator device 14 simultaneously through ENT anatomy to a structure to be dilated. Once the flexible distal portion 22 of dilator 14 is located within the structure to be dilated, plunger 28 may be depressed by the user to inflate balloon 34 and thus dilate the structure. System 10 and the method for using it will be described in greater detail below.

Figure 1B:
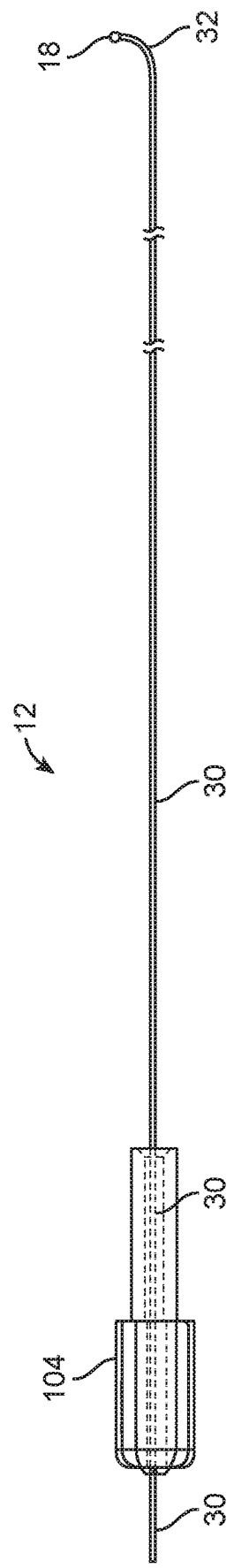
FIG. 1B is a side view of a seeker device coupled with a seeker locking member of the dilation system of FIG. 1A.

Referring to FIG. 1B, seeker device 12 is shown in more detail. As mentioned above, seeker 12 includes a proximal shaft portion 30, elastic distal portion 32 and atraumatic distal tip 18, which in this embodiment is ball-shaped but may alternatively have any other suitable form to prevent tissue trauma as seeker 12 is advanced through anatomy. In some embodiments, proximal shaft 30 is stiffer/more rigid than elastic distal portion 32, but it need not have any particular amount of rigidity. In fact, in some embodiments proximal shaft 30 is fairly flexible and thin. In some embodiments, for example, proximal shaft 30 may be used to advance seeker 12 through ENT anatomy, such as through the nasal cavity, past the turbinates, middle meatus, etc. In such embodiments, proximal shaft 30 may be sufficiently rigid to provide a desirable amount of pushability and/or torqueability. In an alternative embodiment, however, seeker 12 may extend through rigid shaft 20 of dilator device 14 and be locked to handle 16, and thus rigid shaft 20 and handle 16 provide all the needed pushability and torqueability. In these embodiments, proximal shaft 30 may be quite thin, in order to fit conveniently through the inner lumen of dilator device 14, and may also be relatively floppy. For example, in some embodiments, proximal shaft 30 may have a diameter of between about 0.8 mm and about 1.5 mm, and elastic distal portion 32 may have a diameter of between about 0.4 mm and about 1.0 mm.

Proximal shaft 30 and distal portion 32 may also have any suitable cross-sectional shape, and in some cases they may each have a different cross-sectional shape, such as but not limited to round, ovoid, rectangular or triangular. Non-round cross-sectional shapes, such as ovoid or rectangular, may allow distal portion 32 to be more flexible in some directions than in other directions. Additionally, proximal shaft 30 and distal portion 32 may have any suitable lengths, and in fact their lengths may vary considerably between different embodiments, depending on what part of the human anatomy seeker 12 is designed to access. In some embodiments, for example where seeker 12 is designed for accessing the paranasal sinuses or Eustachian tubes, proximal shaft 30 may have a length of up to about 120 mm, and elastic distal portion may have a length of up to about 40 mm. In some embodiments, more specifically, elastic distal portion may be between about 20 mm and about 30 mm long, and in one embodiment about 25 mm long.

In various embodiments, seeker 12 may be made of any suitable material or materials. In one embodiment, for example, seeker 12 may be made of only one material and may be formed as a one-piece, monolithic structure. In other embodiments, proximal shaft 30 may be made of a first material, and elastic distal portion 32 may be made of a second material. Atraumatic distal tip 18 may be made of the same material as proximal portion 30, the same material as elastic distal portion 32, or a different, third material. Generally, therefore, various embodiments of seeker 12 may be made of anywhere from one piece of one type of material to three pieces of three different types of material, or any combination thereof. Some embodiments may include one or more additional materials as well, such as a coating on atraumatic tip 18 or elsewhere. For example, in some embodiments, proximal shaft 30 may be made of Nitinol, stainless steel, titanium, PEEK, or any other suitable metal or polymer. Elastic distal portion 32 may be made of an elastic, super-elastic or shape-memory material, such as but not limited to Nitinol, a copper-aluminum-nickel alloy, a shape-memory polymer, spring stainless steel, an elastic polymer, or any other suitable elastic, super-elastic or shape-memory metal or polymer. In one embodiment, all of seeker 12 is made of Nitinol, and proximal shaft portion 30 simply has a larger outer diameter than elastic distal portion 32. Distal tip 18 is also made of Nitinol in this embodiment, but is formed as a ball shape.

Distal atraumatic tip 18 may have any suitable shape and size and may be made of any suitable material, according to various embodiments. Although distal tip 18 is shown as ball-shaped in many of the figures of this application, it may alternatively be ovoid, triangular, square, oblong, pear-shaped, asymmetrical, etc. In some embodiments, the atraumatic distal tip 18 may simply be a widened, blunt end of elastic distal portion 32. Tip 18 may have a diameter of between about 1 mm and about 2 mm, in some embodiments. Distal tip 18 may be formed in any suitable way. For example, in some embodiments, tip 18 may be a separate piece of material, such as a metal ball, which is attached to the distal end of elastic distal portion 32 by welding, adhesive or the like. In other embodiments, distal tip 18 may simply be an extension of the same piece of material used to make elastic distal portion 32, and it may be molded or otherwise formed into the desired atraumatic shape. In some embodiments, distal tip 18 may be coated, for example it may be a Nitinol ball covering with a thin polymeric coating. In some embodiments, the coating may be hydrophilic, to potentially reduce friction of distal tip 18 as it moves through anatomical passageways.

Figure 1C:
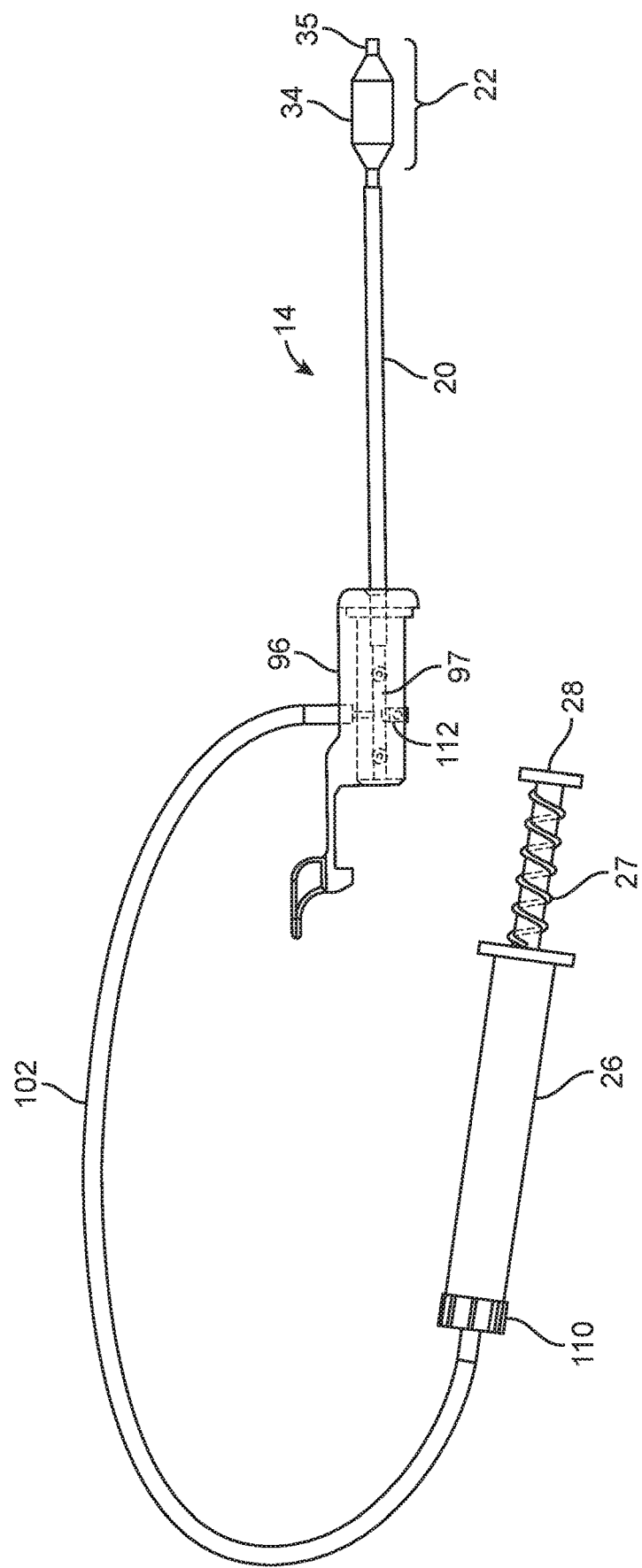
FIG. 1C is a side view of a dilator device coupled with an inflation tube and inflation device of the dilation system of FIG. 1A.
Figure 1D:
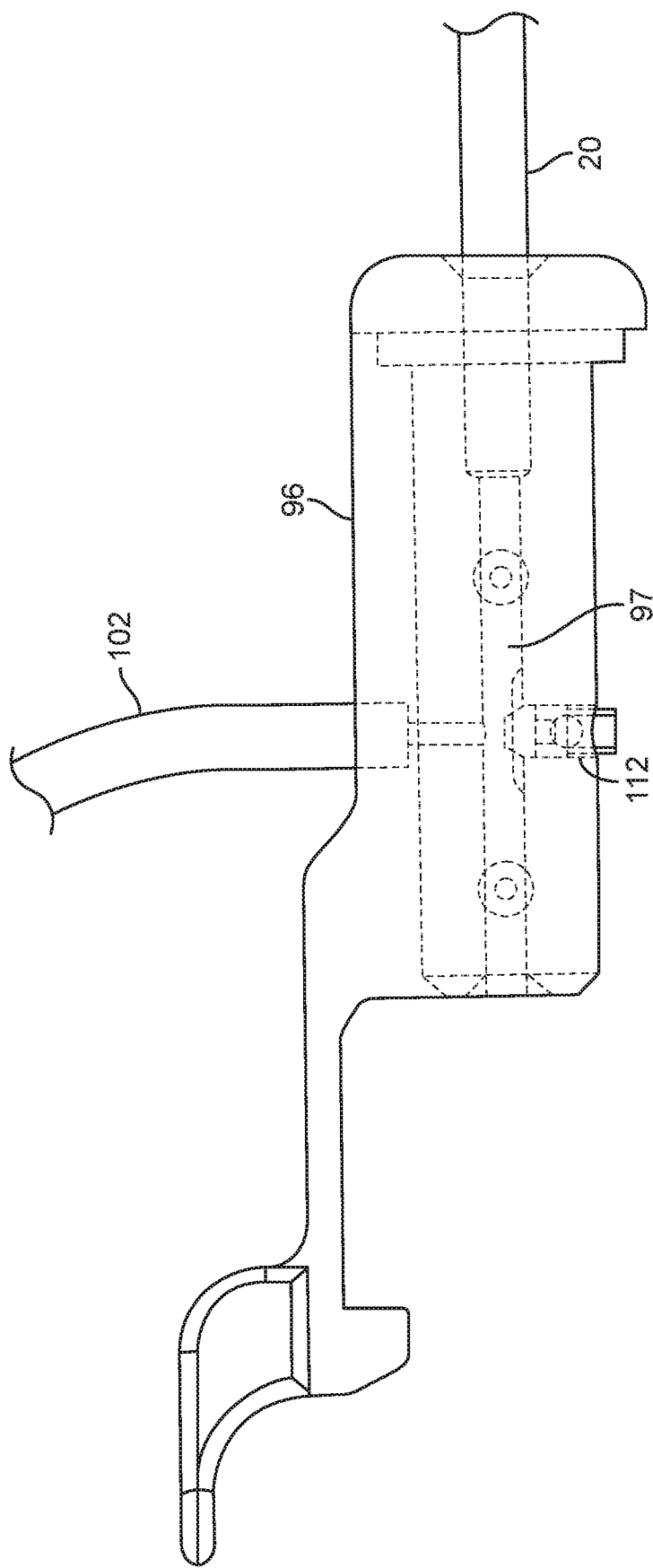
FIG. 1D is a side view of a connector hub of the dilation system of FIG. 1A.

Referring now to FIGS. 1C and 1D, dilator device 14, inflation device 26 and inflation tube 102 are illustrated in more detail. Dilator device 14 may include coupling hub 96 at its proximal end, which is shown in greater detail in FIG. 1D. Dilator device also includes proximal shaft 20 and flexible distal portion 22, the latter of which includes dilation member 34 (or "inflatable balloon") and flexible shaft 35. In alternative embodiments, dilator device 14 may include any alternative suitable dilation member, such as mechanical expanders or the like. Although the description herein focuses on an inflatable balloon embodiment, any other dilation member may be used in alternative embodiments. In the embodiment shown, proximal shaft 20 is rigid and is attached to connector hub 96, which is designed to connect dilator device 14 to handle 16. In alternative embodiments, proximal shaft 20 may be flexible, and in that case proximal portion 30 of seeker 12 may be more rigid, to provide pushability/torqueability to the combined seeker/dilator. Flexible distal portion 22 is sufficiently flexible so that it will conform, at least partially, to the default curved shape of elastic distal portion 32 of seeker 12.

Proximal shaft 20, flexible distal portion 22 and dilation member 34 may be made of any suitable materials. For example, in one embodiment, proximal shaft 20 is formed of a stainless steel (or other metal) hypotube, flexible shaft 35 is made of a polymer, and dilation member 34 is made of PTFE. This is only one example, however. The various parts of dilator device 14 may have any suitable dimensions, according to various embodiments. For example, in some embodiments, proximal shaft may have an outer diameter of between about 1.5 mm and about 3.5 mm, and flexible shaft 35 may have an outer diameter of between about 1.0 mm and about 2.5 mm. Inflatable balloon 34, according to various embodiments, may have an inflated diameter of between about 4.0 mm and about 8.0 mm and a length of between about 5.0 mm and about 40 mm.

As illustrated in FIGS. 1A and 1C, inflation tube 102 is connected at one end to connector hub 96 and at opposite end to an inflation connector 110, which may be a Luer connector in some embodiment. Inflation connector 110 is designed to connect with inflation device 26. Connector hub 96 may include a pressure release valve 112, such as but not limited to a one-way ball valve, and an inner tube 97 for fluidly connecting the inflation lumen of dilator device 14 with inflation tube 102. In some embodiments, inflation device 26 is a spring loaded syringe, with a distal end that connects directly to inflation connector 110. Inflation device 26 may be provided as a custom-built component of dilation system 10, or alternatively in some embodiments an off-the-shelf syringe may be compatible with system 10.

Figure 1E:
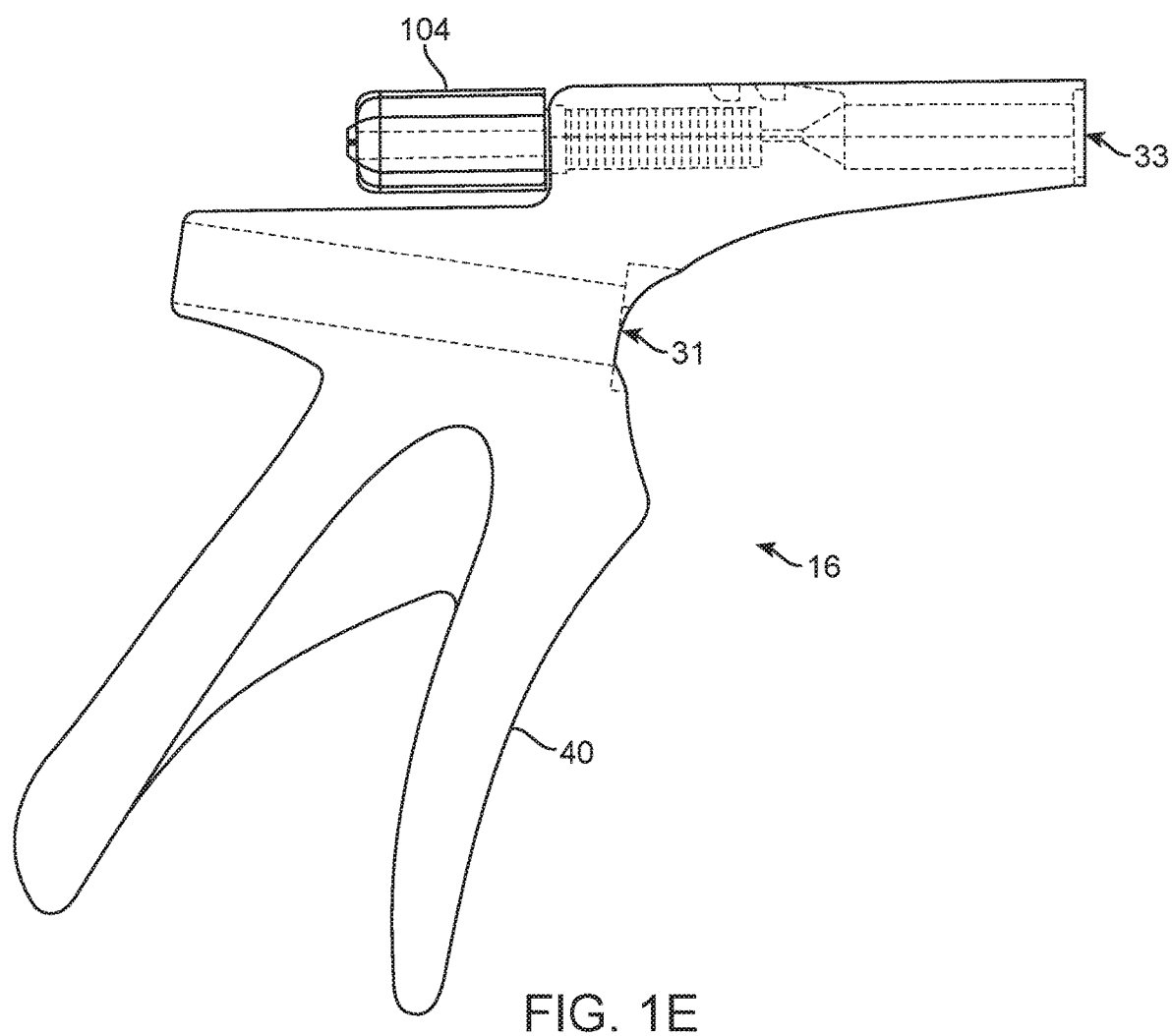
FIG. 1E is a side view of a handle of the dilation system of FIG. 1A.

FIG. 1E shows handle 16 in further detail. The outer shell of handle 16 is illustrated partially transparently in FIG. 1E, so that inner features can be seen. Handle 16 typically includes a hand grip portion 40, which is ergonomically designed for easy holding by a user. In the illustrated embodiment, handle 16 also includes an inflation device housing 31 and a dilator device housing 33, which are of course configured to house inflation device 26 and dilator device 14, respectively. As mentioned above, handle may also include seeker locking mechanism 104, which in this embodiment includes a turning knob that adjusts the inner diameter of the inner lumen running through the knob and thus tightens or loosens seeker locking mechanism 104 over seeker 12.

Figure 1F:
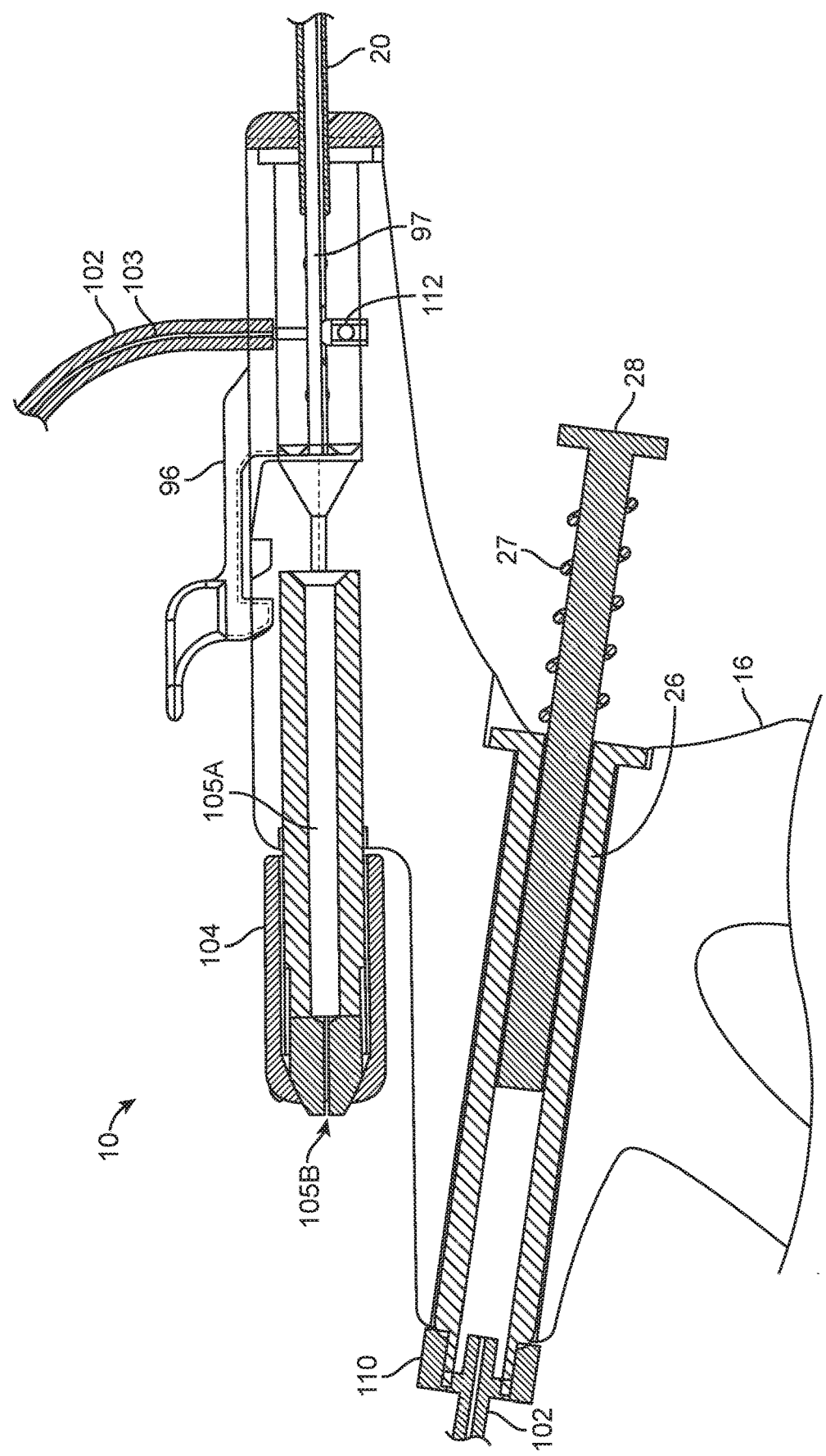
FIG. 1F is a side, cross-sectional view of a portion of the dilation system of FIG. 1A.

FIG. 1F shows a portion of dilation system 10 in a side, cross-sectional view. This view illustrates an inner lumen of inflation tube 102, which connects fluidly with an inflation lumen in inner tube 97 of dilator device 14. FIG. 1F also shows an inner lumen 105A, 105B of seeker locking mechanism 104. Seeker 12 passes through inner lumen 105A, 105B, and locking mechanism 104 is turned to tighten (or loosen) inner lumen 105B to lock seeker 12 into (or unlock it from) locking mechanism 104. Once seeker 12 is locked into locking mechanism 104, its proximal portion will not be able to move, relative to handle 16. Connector hub 96, in turn, locks dilator device 14 to handle 16, so that when assembled, handle 16, dilator device 14, seeker 12 and inflation device 26 are connected together in a fixed manner for a procedure. Therefore, in use, dilator device 14 and seeker 12 are advanced together, as one unit, into the patient's ENT anatomy (or other anatomy). When elastic distal portion 32 of seeker 12 is in a desired position for performing a dilation, inflatable balloon 34 will also be in the desired position, and at no time during the procedure is balloon 34 advanced or retracted over seeker 12. This is significantly different from many, if not all, currently available ENT balloon dilation systems, in which the balloon is typically advanced over a guidewire or other guiding structure to the ostium of the sinus or other structure to be dilated. This difference is significant, because it simplifies the access and dilation process and thus likely reduces user error and balloon wear and tear.

Figure 1I:
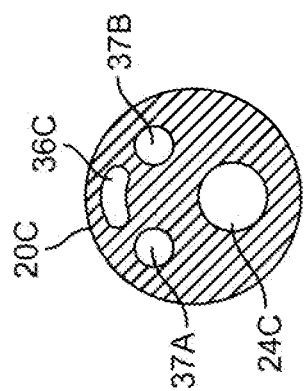
FIGS. 1G-1I are front, cross-sectional views of three different embodiments of a shaft of the dilator device of the dilation system of FIG. 1A, illustrating three different configurations for lumens of the shaft, according to three alternative embodiments.
Figure 1H:
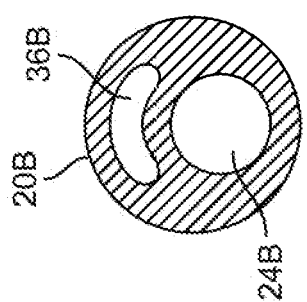
Figure 1G:
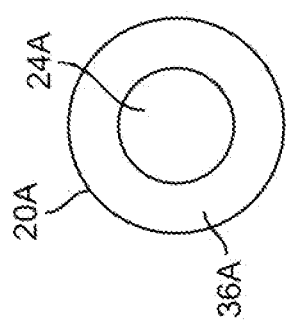

FIGS. 1G-1I are front, cross-sectional views of three alternative embodiments of proximal shaft 20 of dilator device 14. Proximal shaft 20, in various embodiments, will typically include two lumens—inner lumen 24 configured for passage of seeker 12 and an inflation lumen for passage of inflation fluid into balloon dilation member 34. As illustrated in FIG. 1G, in one embodiment, a proximal shaft 20A may include an inner lumen 24A that is located coaxially (or "concentrically") within an inflation lumen 36A. As shown in FIG. 1H, in an alternative embodiment, a proximal shaft 20B may include an inner lumen 24B and an inflation lumen 36B that are located beside one another. As shown in FIG. 1I, in an another alternative embodiment, a proximal shaft 20C may include an inner lumen 24C and an inflation lumen 36C that are located beside one another, and it may additionally include a camera fiber lumen 37A, an irrigation lumen 37B and/or any other suitable lumens or combinations of lumens. Inflation lumens 36A-36C extend into inflatable balloon 34, and inner lumens 24A-24C extend through balloon 34, such as through flexible shaft 35, to allow for passage of seeker 12.

Figure 2A:
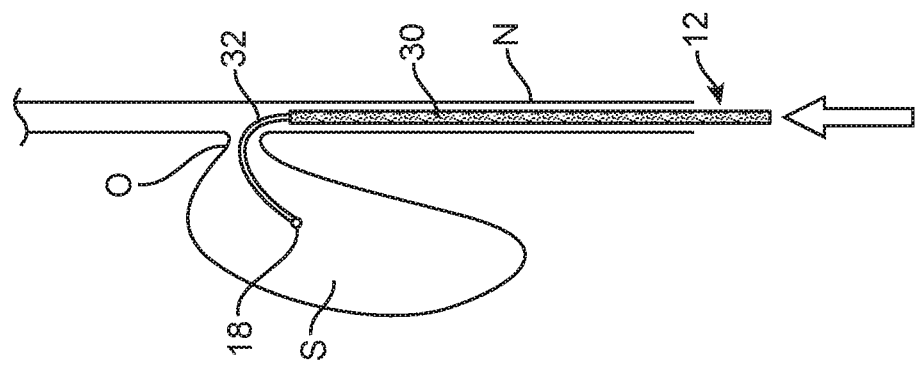
FIGS. 2A-2C are diagrammatic illustrations of a nasal cavity and paranasal sinus, showing a method for accessing the sinus with an elastic distal portion of a seeker, according to one embodiment.
Figure 2B:
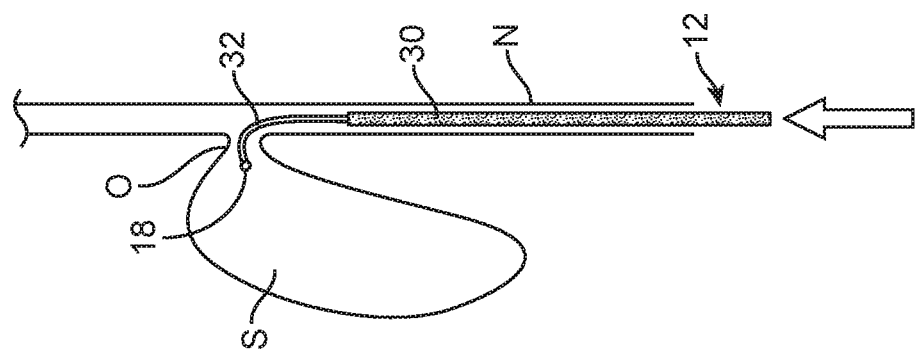
Figure 2C:
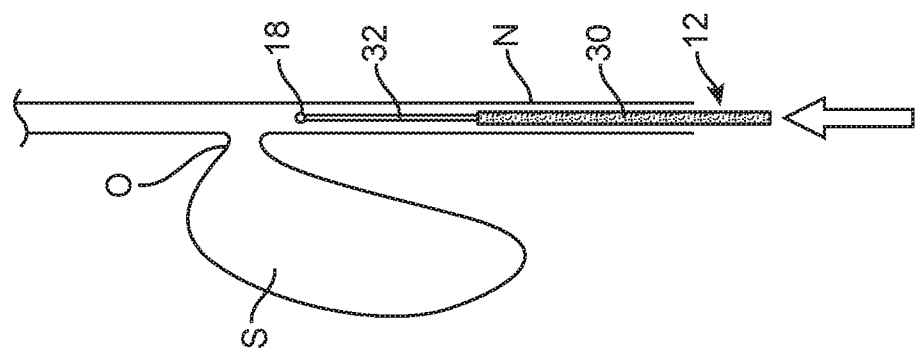

Referring now to FIGS. 2A-2C, a simplified method for advancing seeker 12 to a desired anatomical location is illustrated. In some embodiments, seeker 12 is part of seeker/dilator system 10, while in alternative embodiments, seeker 12 may be used alone as a tool for accessing an anatomical structure or location. FIGS. 2A-2C show seeker 12 being advanced by itself, but this method applies equally to the advancement of seeker 12 as part of seeker/dilator system 10. For example, FIGS. 2A-2C illustrate, in a simplified diagram, a nasal cavity N, a maxillary paranasal sinus S and an ostium O of the sinus S. The nasal cavity N, in particular, is illustrated diagrammatically, to emphasize the narrowness of the typical nasal cavity. In reality, a nasal cavity has many different, protruding anatomical structures, such as the turbinates, meatus, ethmoid sinus, and the like. These structures make advancing a conventional surgical tool through the nasal cavity challenging, but seeker 12 helps facilitate access through such tight passages.

As is illustrated in FIG. 2A, as seeker 12 is advanced through the tight, narrow anatomical passageway of the nasal cavity N, elastic distal portion 32 is typically constrained in a first, constrained configuration. In some embodiments, as illustrated, this configuration may be relatively straight. In other embodiments, elastic distal portion 32 may have a curve in it, typically in one plane, in its constrained configuration. Ball-shaped tip 18 is used as an atraumatic device for pushing through the anatomy. As seeker 12 is further advanced through the nasal cavity N, as in FIG. 2B, elastic distal portion 32 encounters the ostium O and is able to begin resuming its default shape. As it does so, ball-shaped tip 18 may actually spring or "pop" through the ostium O into the maxillary sinus S. As shown in FIG. 2C, as seeker 12 is advanced farther into the nasal cavity N, distal portion 32 is free to resume even more of its default configuration and thus move farther into the maxillary sinus S. Therefore, the curved shape of elastic distal portion 32 means that as proximal portion 30 of seeker 12 is pushed in a posterior direction by the user, distal portion 32 advances sideways, into the sinus S. A similar technique may be used to access any frontal or sphenoid sinus, an opening into an ethmoid sinus, a Eustachian tube, or the like. For each different anatomical target, a differently shaped seeker 12 may be used. This elastic or shape-memory function of distal portion 32, along with its curved shape, is much different than currently available seekers, which are typically rigid, and thus often very difficult to advance through tight, anatomical passageways. Malleable seekers are little better, because although a physician may adjust their shape outside of the patient, they do not change shape inside the patient and thus must be pushed through tight spaces the same way as rigid seekers. Seeker 12 described herein has the advantage of changing shape inside the patient, from a relatively straight, constrained configuration, to a curved, default configuration, where the curve (or curves) in the default configuration are specifically designed for a particular anatomical target. Seeker 12 also has the advantage of having a distal portion that moves in a direction that is different than the direction the proximal portion is being advanced in.

Figure 3C:
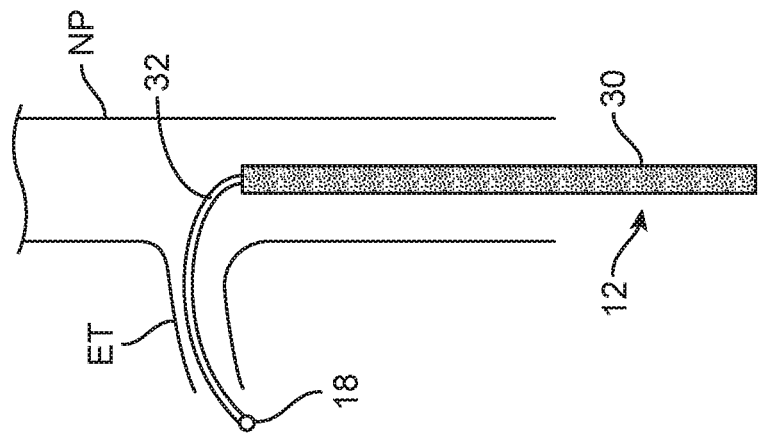
FIGS. 3A-3C are diagrammatic illustrations of a nasopharynx and Eustachian tube, showing a method for accessing the Eustachian tube with an elastic distal portion of a seeker, according to one embodiment.
Figure 3B:
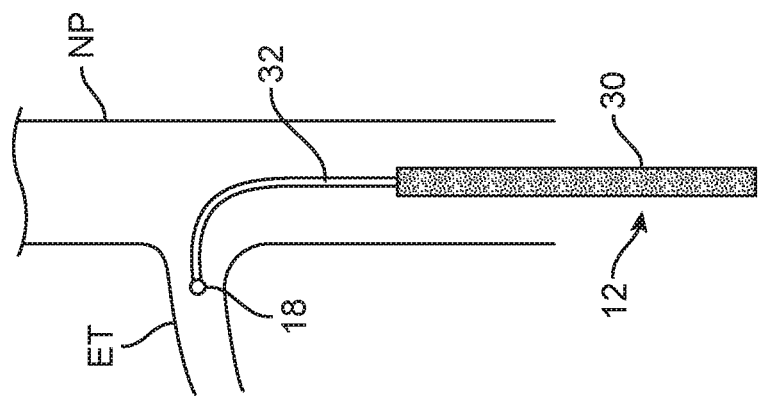
Figure 3A:
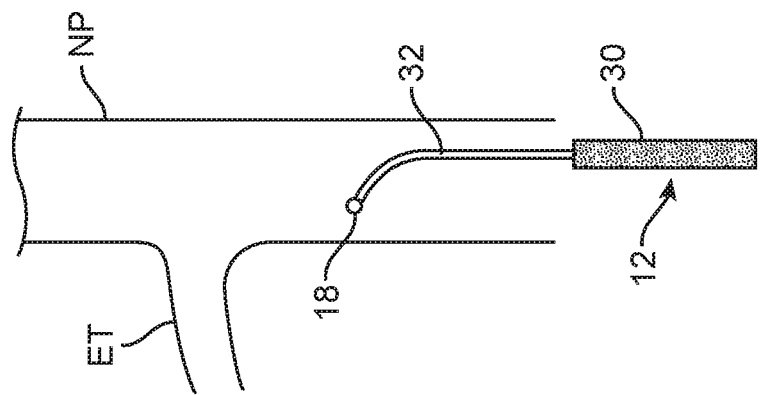

With reference now to FIGS. 3A-3C, a similar method is illustrated for accessing a Eustachian tube ET. Here, seeker 12 is advanced posteriorly through the nasopharynx NP toward the Eustachian tube ET. Again, as proximal shaft 30 of seeker 12 is advanced farther posteriorly, as in FIG. 3B, elastic distal portion 32 begins to advance sideways into the Eustachian tube ET. Finally, as illustrated in FIG. 3C, as the user continues to advance proximal portion 30 of seeker 12 farther posteriorly, elastic distal portion 32 moves farther sideways into the Eustachian tube ET.

Figure 4A:
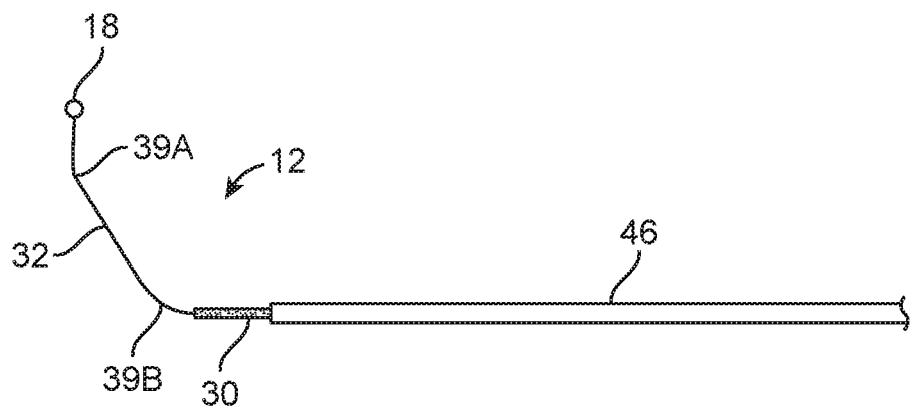
FIGS. 4A-4C are side views of a sheath and an elastic distal portion of a seeker device, illustrating a method for enclosing the elastic distal portion in the sheath for advancement through anatomy, according to one embodiment.
Figure 4B:
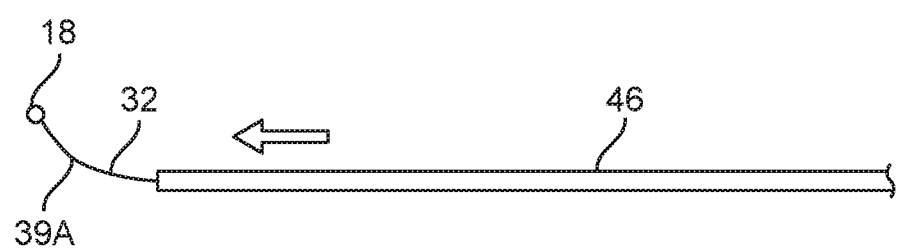
Figure 4C:

Referring now to FIGS. 4A-4C, one optional additional feature (and method step), which is not illustrated in FIGS. 2A-3C, is a retractable sheath 46, which may be disposed over seeker 12 during advancement through the anatomy. Again, sheath 46 may be used with seeker 12 alone or may alternatively be used to cover seeker 12 and dilator 14 during advancement of system 10 into a patient's anatomy. Sheath 46 may act to hold distal portion 32 in its relatively straight, constrained configuration for advancement and then may be retracted proximally over seeker 12, to allow distal portion 32 to assume its default configuration at the target location. FIGS. 4A-4C illustrate that process in reverse, in other words the advancement of sheath 46 over seeker 12, for example as might be done before initial advancement of seeker 12 into the anatomy during a procedure. FIG. 4A shows sheath 46 retracted proximally, so that distal portion 32 and a small part of proximal portion 30 are outside of sheath. As illustrated in this figure, elastic distal portion 32 may include a first or distal curve 39A and a second or proximal curve 39B, both of which are in the same plane in this embodiment. As mentioned previously, alternative embodiments of elastic distal portion 32 may have only one curve, multiple curves in multiple planes, more than two curves, etc. The embodiment illustrated in FIG. 4A is similar to that shown in FIG. 7D, which might be used to access a frontal maxillary sinus, for example. FIG. 4B shows sheath 46 advanced farther over seeker 12, so that only distal curve 39A is exposed. When the illustrated method is reversed and sheath 46 is retracted proximally over seeker to expose elastic distal portion 32, distal curve 39A will be exposed first and proximal curve 39B will be exposed second, as sheath 46 is further retracted. FIG. 4C shows only a portion of distal tip 18 protruding out of the end of sheath 46, as might be the configuration during advancement through the anatomy to a target area. Sheath 46 may be made of any suitable material and have any suitable length to allow the user to retract it when desired. For example, in one embodiment, sheath 46 may be a stainless steel hypotube. Sheath 46 may help facilitate advancement of seeker 12 through anatomy and help prevent distal portion 32 from getting caught on any anatomical structures during advancement.

Sheath 46 may also be included as part of dilation system 10 of FIG. 1A, in which case it also functions to protect inflatable balloon 34 from damage during advancement through the anatomy.

Figure 5A:
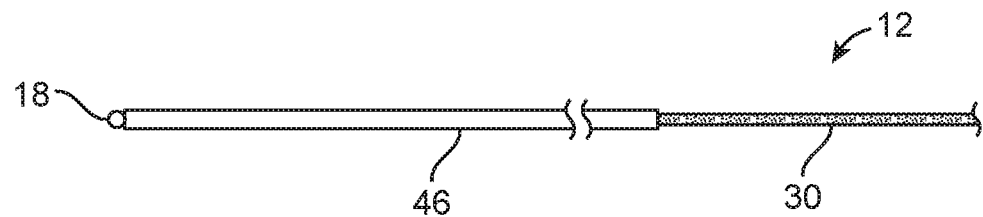
FIGS. 5A-5C are side views of a sheath and an elastic distal portion of a seeker device, illustrating a method for retracting the sheath to expose the elastic distal portion, according to one embodiment.
Figure 5B:
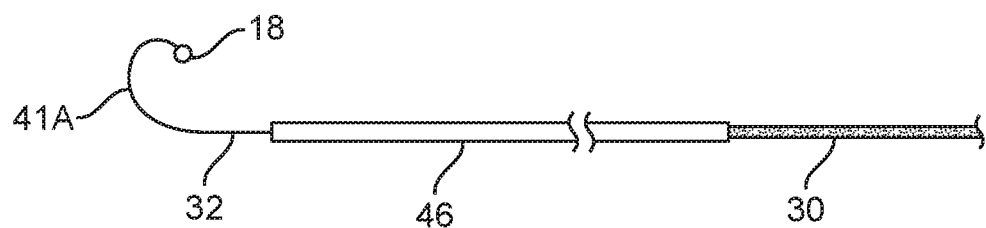
Figure 5C:
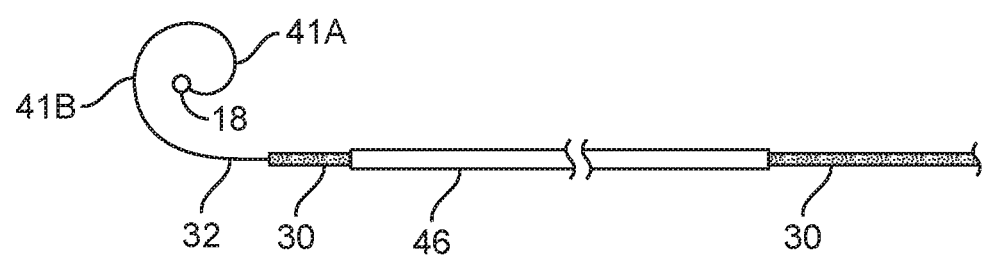

FIGS. 5A-5C illustrate the reverse of the method just described, with a different embodiment of seeker 12, this one configured for accessing a maxillary paranasal sinus. This illustrated method is the type that may be performed after seeker 12 and sheath 46 have been advanced through a portion of the nasal canal or other anatomy to a site of interest. Sheath 46 is then retracted over seeker 12 to expose elastic distal portion 32. As shown in FIG. 5A, seeker 12 may be advanced with only distal tip 18 (or a portion of distal tip 18) protruding out of the distal end of sheath 46. FIG. 5B shows sheath 46 partially retracted proximally, to expose a first, distal curve 41A of elastic distal portion 32. Distal curve 41A may be exposed, for example, when the distal end of sheath 46 and distal tip 18 of seeker are located near the maxillary sinus ostium. FIG. 5C shows sheath 46 further retracted proximally, to expose a second, proximal curve 41B of elastic distal portion 32. The first part of the retraction of sheath 46 (FIG. 5B) may position distal tip 18 at or near the ostium, and the second part of the retraction of sheath (FIG. 5C) may cause (or help) distal tip 18 to pass through the ostium and into the maxillary sinus. In this illustrated embodiment, distal curve 41A and proximal curve 41B are in the same plane. Alternatively, the two curves 41A, 41B may be in different planes, and in some embodiments, for example, distal curve 41A may bend in the same plane as proximal curve 41B and may also bend out of that plane. For example, such curvature may be similar to that of a corkscrew. Again, these are illustrative embodiments only, and any combination of curves or bends may be included in various embodiments of elastic distal portion. Similarly, the methods of advancing sheath 46 distally over seeker 12 (FIGS. 4A-4C) and retracting sheath 46 proximally over seeker 12 (FIGS. 5A-5C) may be used with many, if not all, of the embodiments described herein.

In alternative embodiments, sheath 46 and seeker 12 of FIGS. 5A-5C may be manipulated differently to achieve access to the maxillary sinus (or other anatomy in other embodiments). For example, in one embodiment, seeker 12 and sheath 46 may be advanced through the nasal cavity with sheath 46 partially retracted and elastic distal portion 32 partially exposed, such as the configuration shown in FIG. 5B. Once an initial area of interest within the anatomy is reached, sheath 46 may be further retracted to further expose elastic distal portion 32, as in FIG. 5C, and thus cause distal tip 18 to extend into the sinus. Alternatively, during advancement or once the initial area of interest is reached, sheath 46 may be advanced further over elastic distal portion 32, for example to a configuration as in FIG. 5A, and seeker 12 and sheath 46 may be repositioned within the nasal cavity before retracting sheath 46 again to expose elastic distal portion 32. In general, any of the embodiments described herein of methods for accessing, dilating and/or visualizing a paranasal sinus, Eustachian tube or other anatomical target may involve any suitable steps for retracting and/or advancing sheath 46 over seeker 12, for advancing, retracting and/or otherwise manipulating sheath 46 and seeker 12 together, and/or for any other movement or manipulation of sheath 46 and seeker 12.

Figure 6A:
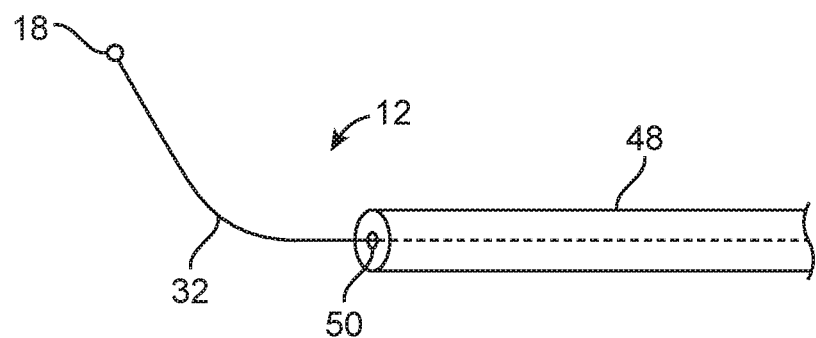
FIGS. 6A-6C are side views of an elastic distal portion of a seeker device and a flexible endoscope, illustrating a method for visualizing a target location by advancing the endoscope over the seeker, according to one embodiment.
Figure 6B:
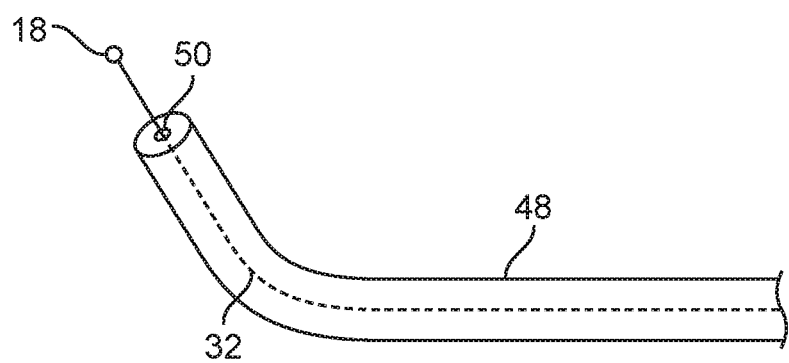
Figure 6C:
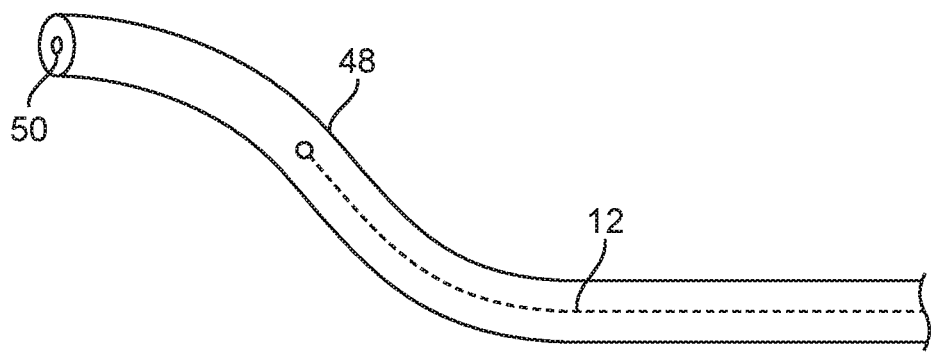

Referring to FIGS. 6A-6C, seeker 12 is shown paired with a flexible endoscope 48, which includes a seeker lumen 50 through which seeker 12 passes. The figures illustrate a method for visualizing a location. FIG. 6A shows seeker 12 advanced so that distal elastic portion 32 has assumed its default shape and distal tip 18 is in a desired location within the patient's body. Flexible endoscope 48 is located over seeker 12, via seeker lumen 50. As illustrated in FIG. 6B, after distal tip 18 of seeker 12 is located in the desired location, flexible endoscope 48 is advanced over elastic distal portion 32. In various embodiments, endoscope 48 may be flexible along its entire length or along only a distal portion of its length. Either way, flexible endoscope 48 is sufficiently flexible so that it will assume, at least partially, the default shape of elastic distal portion 32 when it resides over that portion. Referring to FIG. 6C, endoscope 48 may in some embodiments be further advanced so that a distal portion of it extends beyond distal tip 18 of seeker 12. Endoscope 48 may be used during and/or after any of the illustrated steps to visualize the local anatomy. In other embodiments, endoscope 48 may be advanced less than or more than in the illustrated method embodiment. In one embodiment, endoscope 48 may not be advanced at all, and in some embodiments endoscope 48 and seeker 12 may be fixed, proximally, to a handle, so that they do not move relative to one another. According to various embodiments, any flexible endoscope with a lumen for seeker 12 may be used, such as but not limited to the flexible endoscopes described in U.S. Patent Application Pub. No. 2015/0289754, entitled "Paranasal Sinus Access System," which is hereby incorporate by reference in its entirety.

Figure 7A:
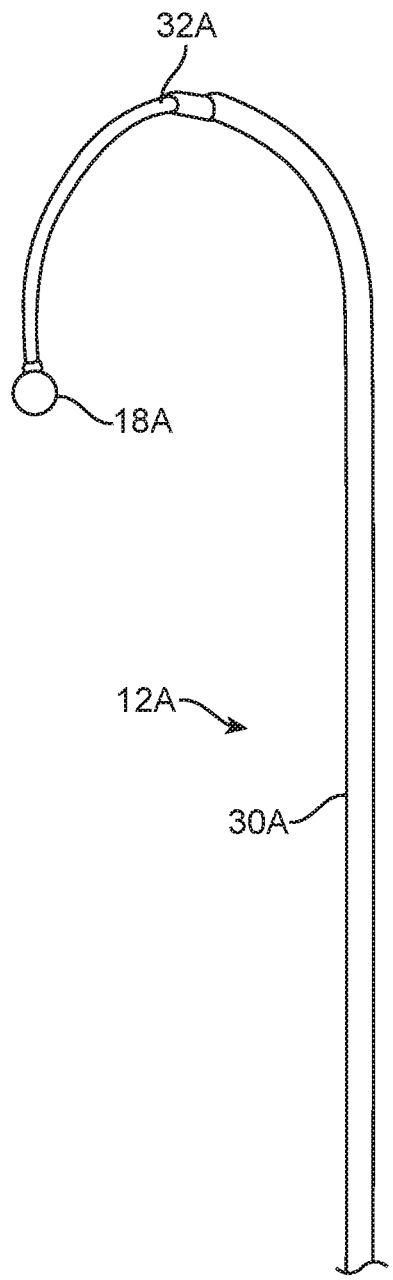
FIGS. 7A and 7B are side and top views, respectively, of a sinus seeker designed for facilitating access to a right maxillary paranasal sinus, according to one embodiment.
Figure 7B:
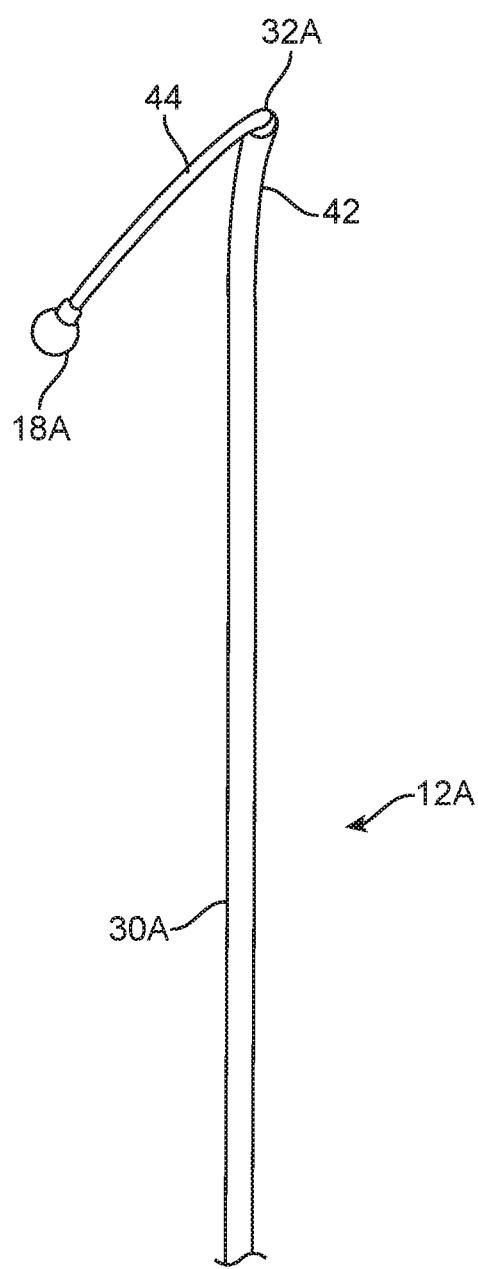
Figure 7C:
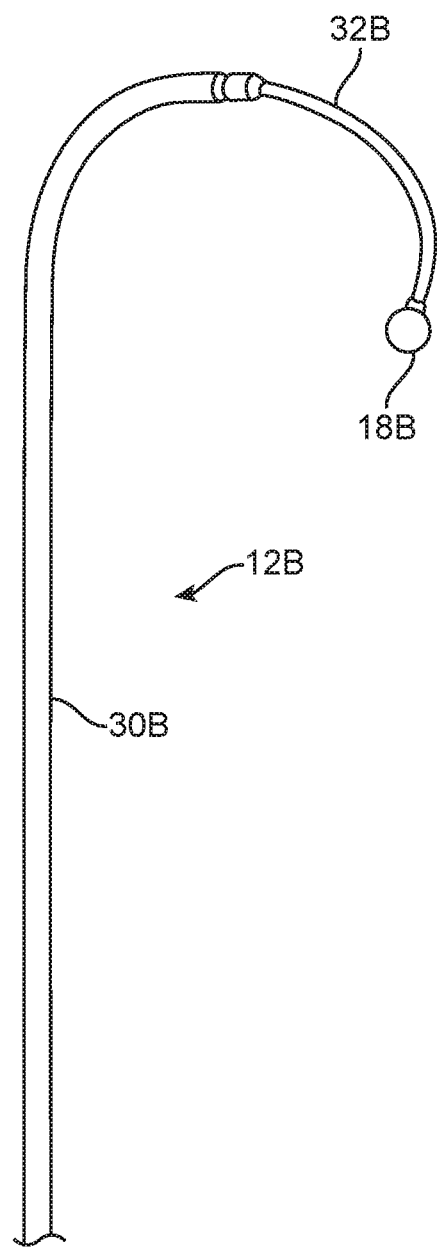
FIG. 7C is a side view of a sinus seeker designed for facilitating access to a left maxillary paranasal sinus, according to one embodiment.
Figure 7D:
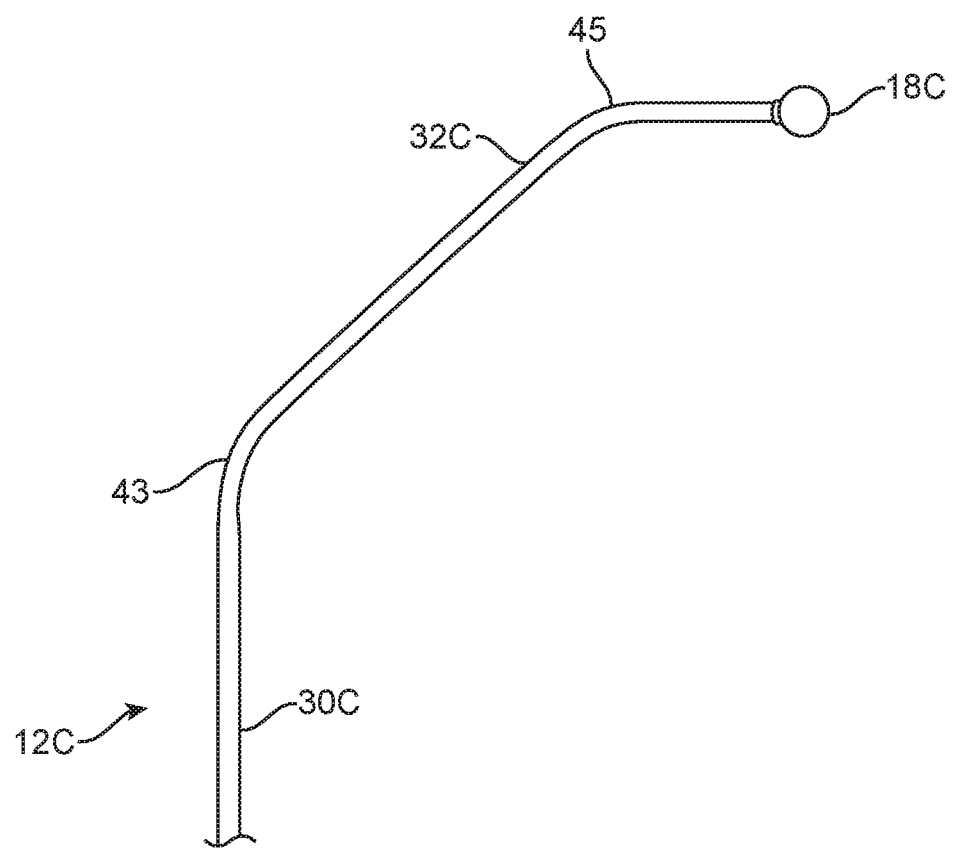
FIG. 7D is a side view of a sinus seeker designed for facilitating access to a frontal paranasal sinus, according to one embodiment.

Referring now to FIGS. 7A-7E, several different embodiments of seeker 12 are illustrated, each having a differently shaped elastic distal portion 32 designed for facilitating access to a specific anatomical area. For example, in the embodiment illustrated in FIGS. 7A (side view) and 7B (top view), seeker 12A is configured to access a right maxillary paranasal sinus. Seeker 12A includes a proximal portion 30A, an elastic distal portion 32A and a ball tip 18A. As illustrated in the top view of FIG. 7B, elastic distal portion 32A includes a first, proximal curve 42 in a first plane and a second, distal curve 44 in a second plane. As mentioned above, in various embodiments, distal portion 32 may have one curve in one plane, multiple curves in one plane or multiple curves in multiple planes. Thus, in some embodiments, elastic distal portion 32 has a "two-dimensional" or flat configuration, while in other embodiments it may have a three-dimensional or multi-plane configuration. In the embodiment of FIGS. 7A and 7B, where elastic distal portion 32A has two curves 42, 44 in two planes, seeker 12 is typically advanced through the nasal cavity with distal portion 32A in a flat configuration, where proximal curve 42 is in its curved configuration and distal curve 44 is held in a constrained, flat configuration by the nasal anatomy. When distal curve 44 is released from constraint, such as by advancing it past constraining anatomy, distal curve 44 resumes its curved shape, thus causing (or facilitating) distal tip 18A to enter the maxillary sinus. Thus, in some embodiments seeker 12A is advanced in a curved configuration and later assumes a more-curved configuration. In other embodiments, seeker 12 is advanced in a relatively straight configuration and later assumes a curved configuration.

Figure 7E:
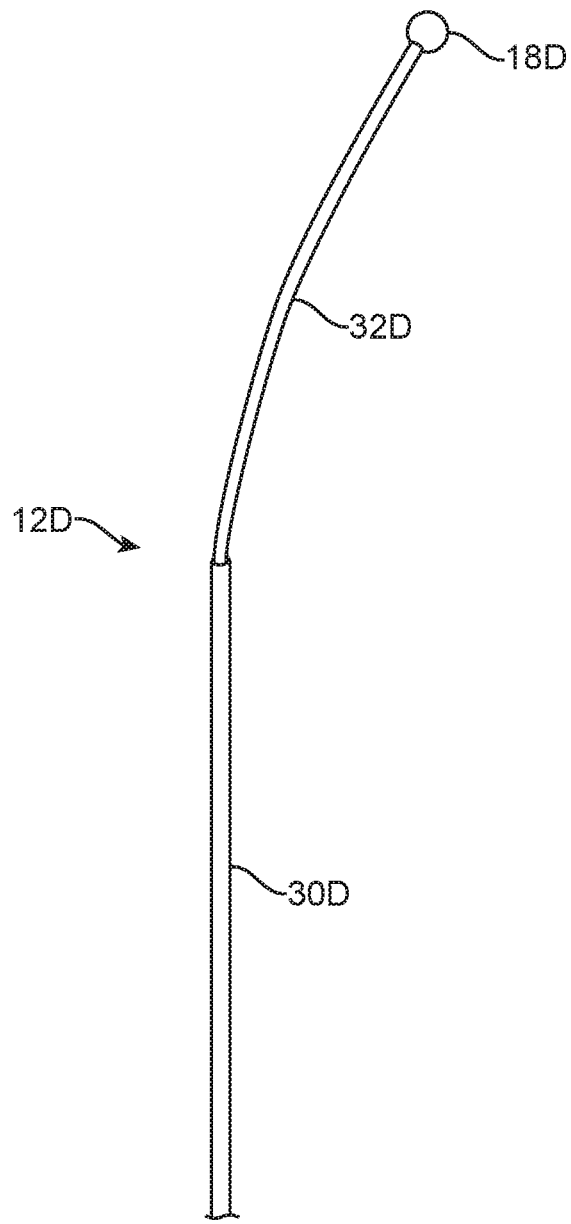
FIG. 7E is a side view of a sinus seeker designed for facilitating access to a Eustachian tube, according to one embodiment.

FIG. 7C is a side view of another embodiment of a seeker 12B, which also includes a proximal portion 30B, an elastic distal portion 32B and a ball tip 18B. This embodiment is approximately a mirror image of the embodiment of FIGS. 7A and 7B and is thus configured to facilitate access to a left maxillary sinus. The embodiment of seeker 12C in FIG. 7D also includes a proximal portion 30C, an elastic distal portion 32C and a ball tip 18C. This embodiment of seeker 12C is configured to access a frontal paranasal sinus and includes a first, proximal curve 43 in a first plane and a second, distal curve 45 in the same first plane. FIG. 7E is a side view of another embodiment of a seeker 12D, which also includes a proximal portion 30D, an elastic distal portion 32D and a ball tip 18D. This embodiment of elastic distal portion 32D is configured for accessing a Eustachian tube. These embodiments are shown for exemplary purposes only, and many other suitable shapes, sizes and configurations are possible.

Figure 8A:
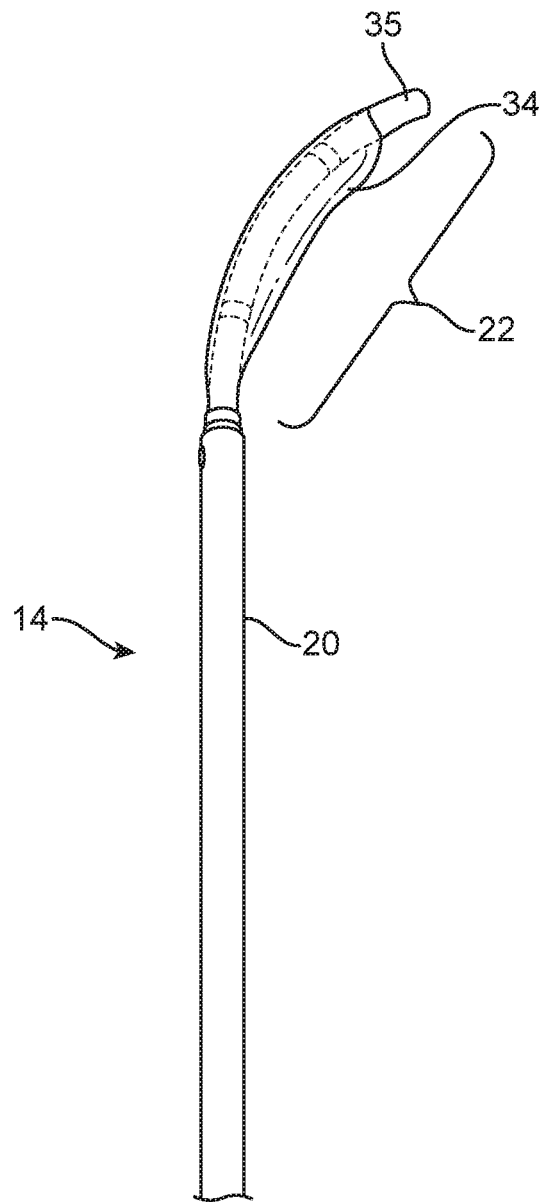
FIGS. 8A-8D are side views of a distal portion of a dilator device, illustrating a method for changing the shape of the flexible distal portion of the device, using a seeker, and dilating and deflating the device, according to one embodiment.
Figure 8B:
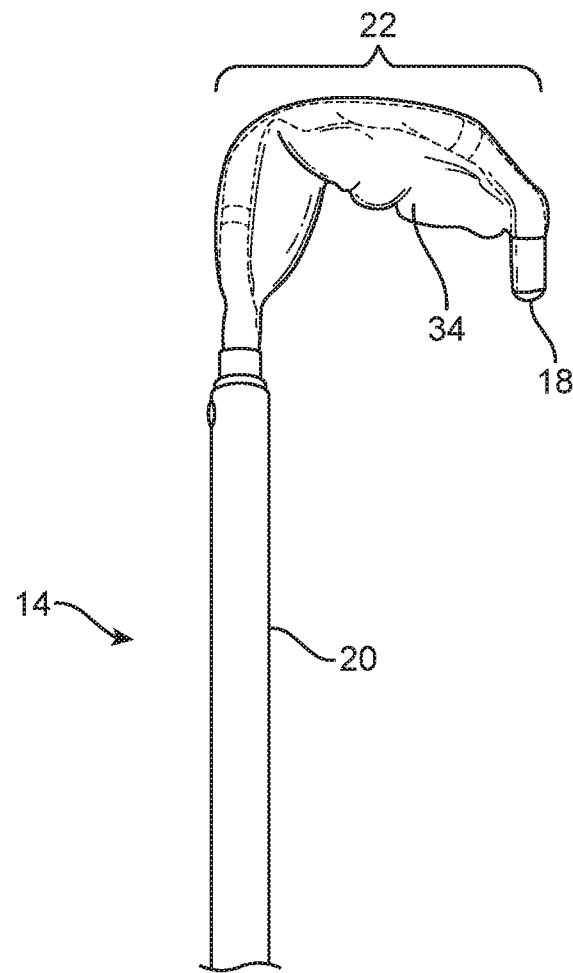
Figure 8C:
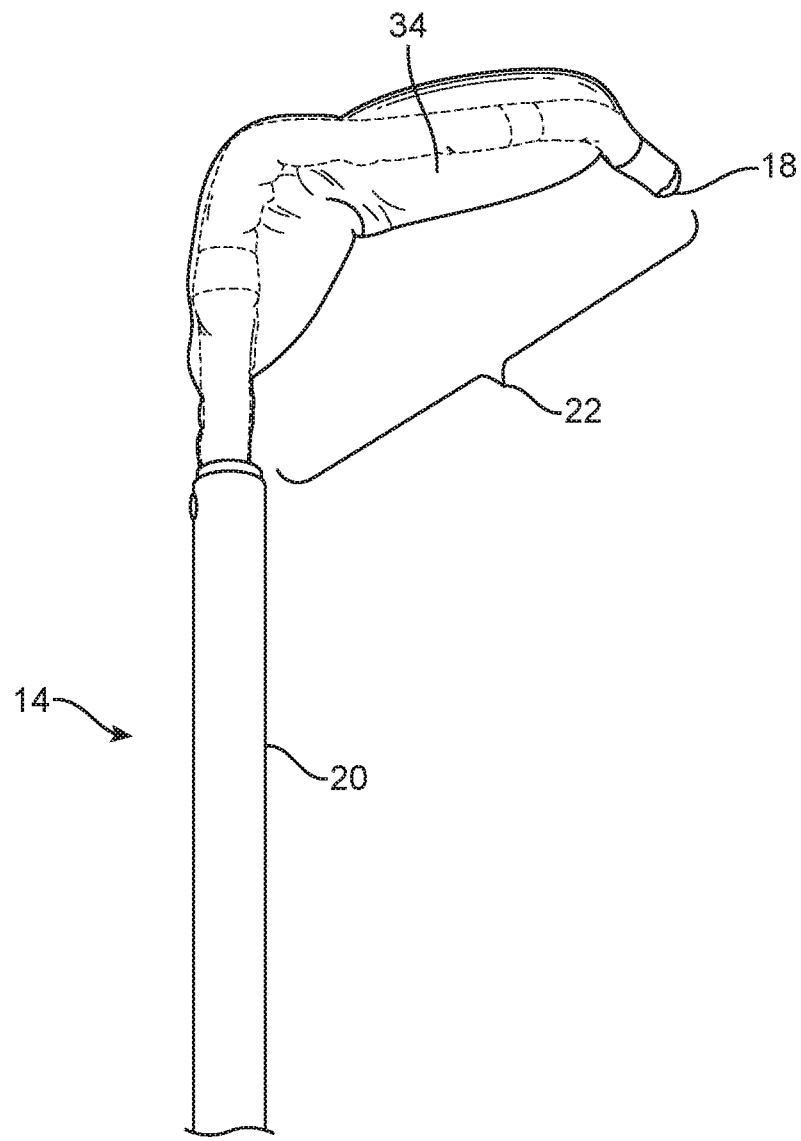
Figure 8D:
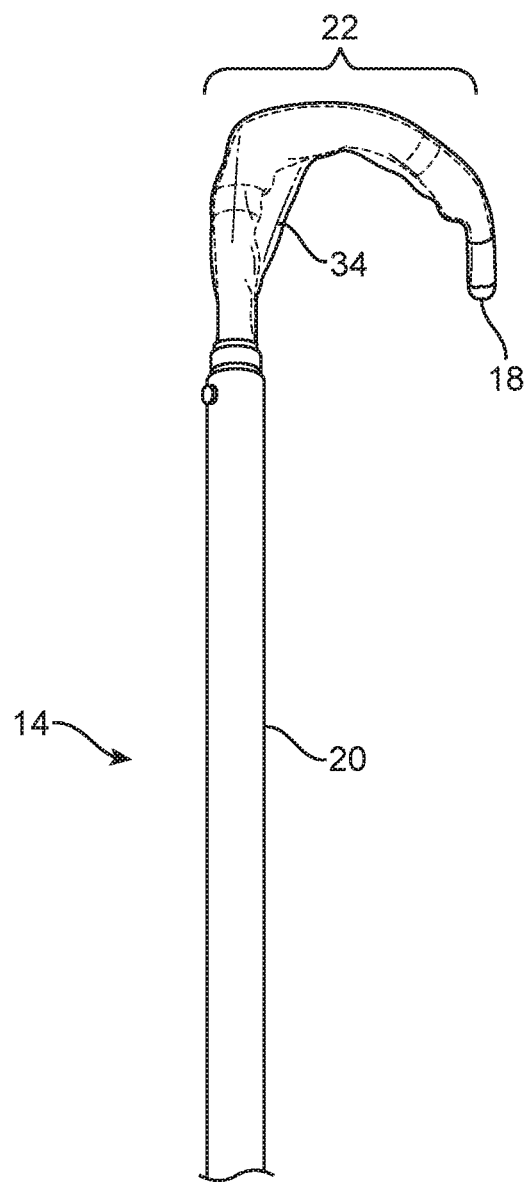
Figure 8E:
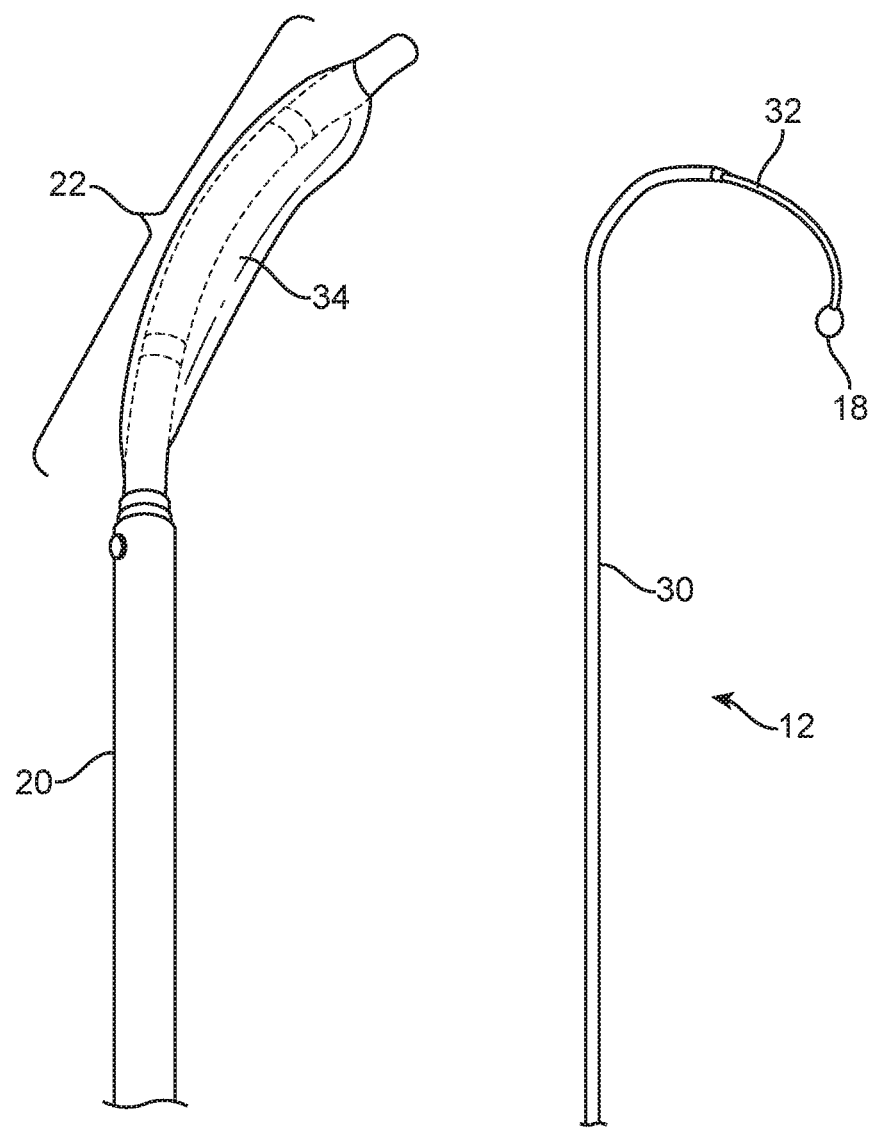
FIG. 8E is a side view of the distal portion of the dilator device of FIGS. 8A-8D, illustrated along with a side view of the seeker device.

Referring now to FIGS. 8A-8E, the pairing of dilator device 14 with seeker 12 is illustrated, along with an inflation of dilation member 34. FIG. 8A illustrates a distal portion of dilator device 14, which includes proximal shaft 20 (in this embodiment a metal hypotube) and flexible distal portion 22, the latter of which includes flexible distal shaft 35 and inflatable balloon 34. In FIG. 8A, seeker 12 has not yet been advanced into the inner seeker lumen of flexible shaft 35 and proximal shaft 20. FIG. 8B illustrates dilator device 14 after seeker 12 has been advanced all the way into dilator device 14, so that only ball-shaped tip 18 protrudes out of the distal end. Obviously, in this figure, flexible distal portion 22 has assumed the curved default shape of elastic distal portion 32 of seeker 12. In FIG. 8C, inflatable balloon 34 has been inflated, as for a dilation procedure, and in FIG. 8D, inflatable balloon 34 has been deflated again, as for removal of dilator device 14 from the patient. FIG. 8E shows dilator device 14 and seeker 12 side-by-side.

Figure 9A:
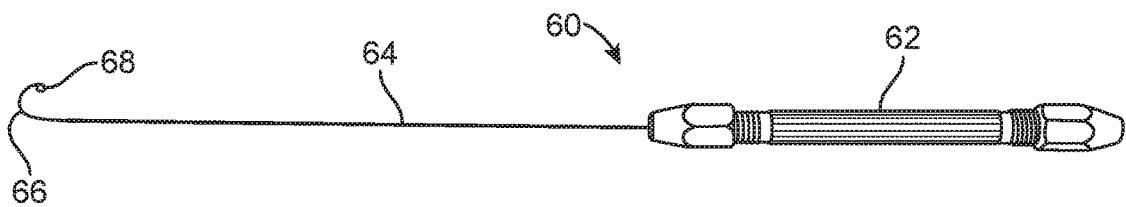
FIGS. 9A and 9B are side views of a seeker (FIG. 9A) and a coupled seeker and dilator (FIG. 9B), according to an alternative embodiment.
Figure 9B:
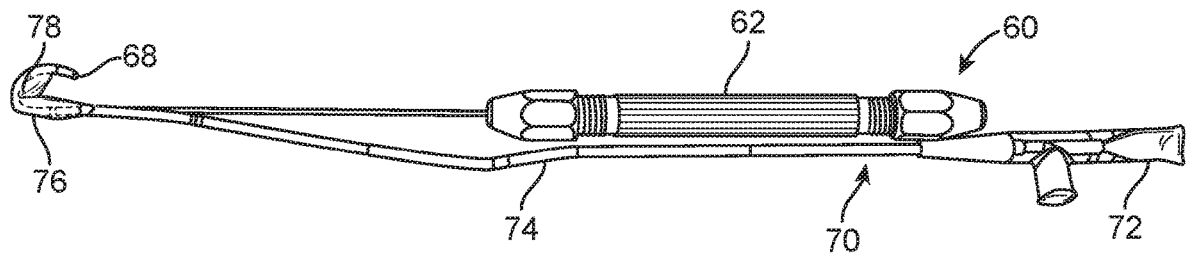

With reference now to FIGS. 9A and 9B, a seeker device 60 and a dilator device 70 are illustrated, according to another embodiment. As best seen in FIG. 8A, the seeker device 60 in this embodiment includes a handle 62, a proximal shaft 64, an elastic distal portion 66 and an atraumatic distal tip 68. All the aspects of this embodiment of seeker 60 may be identical to those of the embodiments described above, but in this case seeker 60 also includes handle 62. Handle 62, of course, may be convenient when seeker 60 is used by itself or with a floppy/flexible dilator device 70, for accessing a paranasal sinus, Eustachian tube or other structure. Alternatively, handle 62 may be a separate component, which may be attached to proximal shaft 64. Handle 62 may be made of any suitable material, such as any metal or polymer, and proximal shaft 64 may be attached to handle 62 by any suitable means.

FIG. 9B shows seeker device 60 coupled with dilator device 70, the latter of which may include a proximal Luer connector 72 (for connecting with an inflation device), a proximal shaft 74, and a flexible distal portion 76 that includes an inflatable balloon 78. In the illustrated embodiment, dilator device 70 includes a rapid exchange seeker lumen (not visible in the drawing), which has a first opening at the extreme distal end of dilator device 70 and a second opening just proximal to flexible distal portion 76. Dilator device 70 is passed over seeker 60 via this rapid exchange seeker lumen, and if necessary dilator device 70 may be swapped out for another dilator device or moved onto a differently shaped seeker device. Proximal portion 74 of dilator device 70 may attach to handle 62 of seeker 60 in some embodiments, by any suitable attachment mechanism. Seeker device 60 and dilator device 70 may be advanced into the patient and used for a dilation procedure in the configuration illustrated in FIG. 9B.

Figure 10A:
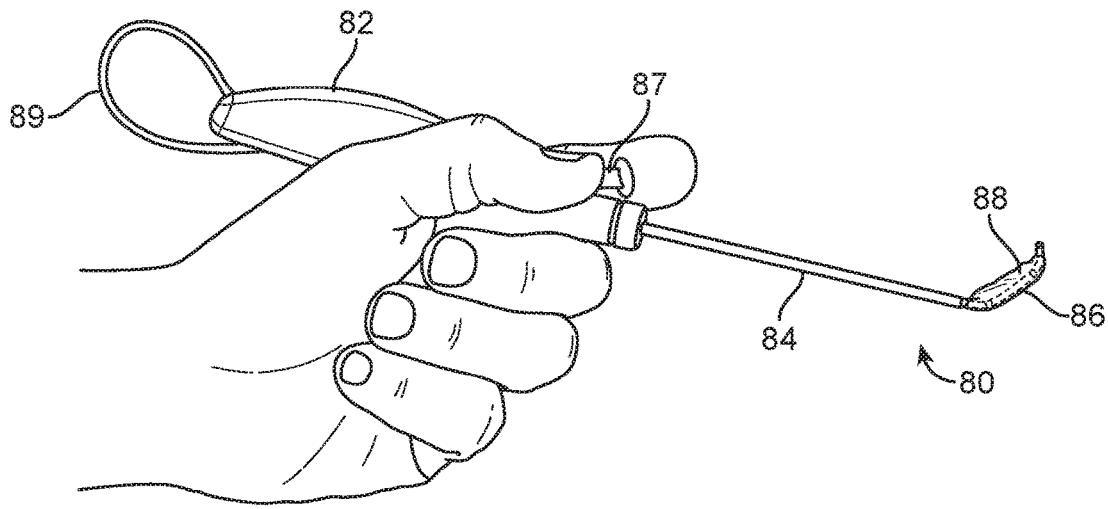
FIGS. 10A and 10B are side views of a combined seeker/dilator device, according to another alternative embodiment.
Figure 10B:
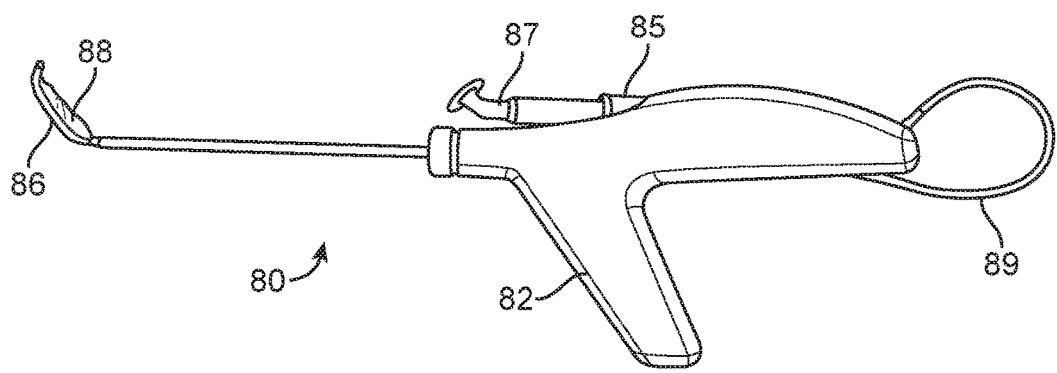

FIGS. 10A and 10B illustrate one embodiment of a combination seeker/dilator device 80. In this embodiment, seeker/dilator 80 includes a handle 82, a rigid shaft 84, a flexible distal portion 86 with an inflatable balloon 88, an inflation member 85 with a plunger 87, and a tube 89 for connecting inflation member 85 with an inflation lumen running through shaft 84 to balloon 88. In this embodiment, the elastic distal portion of the seeker, which is inside flexible distal portion 86 and thus not visible, may be directly attached to shaft 84 or may be attached to a proximal portion of the seeker that runs through shaft 84. As is evident from FIG. 10A, seeker/dilator device 80 may be easily held and manipulated with one hand, and the plunger 87 may be depressed with one finger to inflate balloon 88 and thus dilate an anatomical structure.

Referring now to FIGS. 11A-11I, a method for preparing seeker/dilator system 10 for use is illustrated. (The embodiment of seeker/dilator system 10 is similar to, or the same as, that shown in FIGS. 1A-1F.) As a first step, illustrated in FIGS. 11A and 11B, dilator device 14 may be attached to a handle 16 via connector hub 96. In various embodiments, dilator device 14 may be provided to a user separate from handle 16, so that the user connects the two components as in FIGS. 11A and 11B. Alternatively, the two components 14, 16 may be permanently or removably attached to one another during manufacturing, before providing them to the user.

Figure 11A:
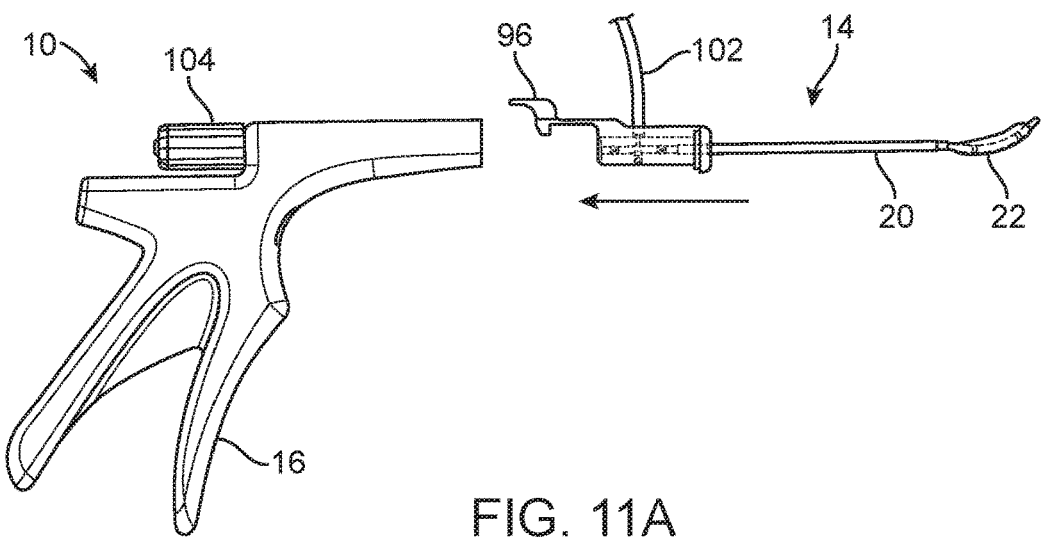
FIGS. 11A-11I are side views of a seeker/dilator system, illustrating a method for preparing the system for use in a patient, according to one embodiment.
Figure 11B:
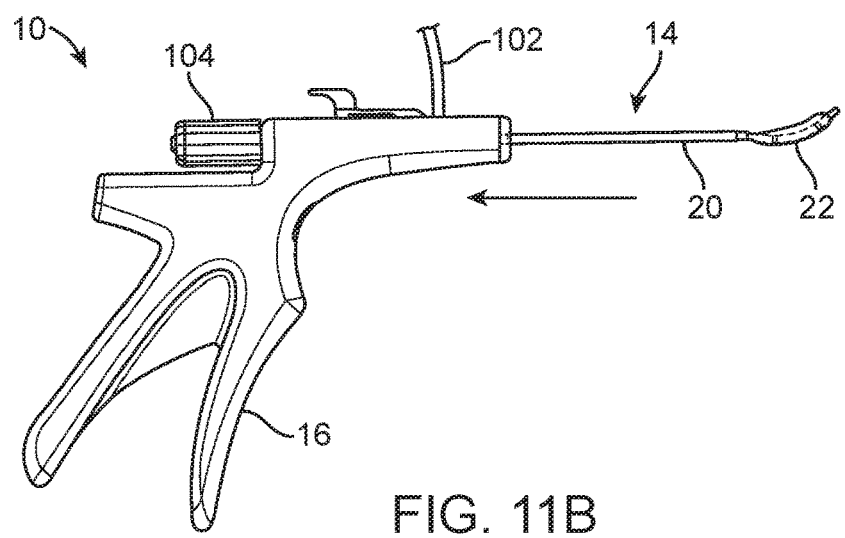
Figure 11C:
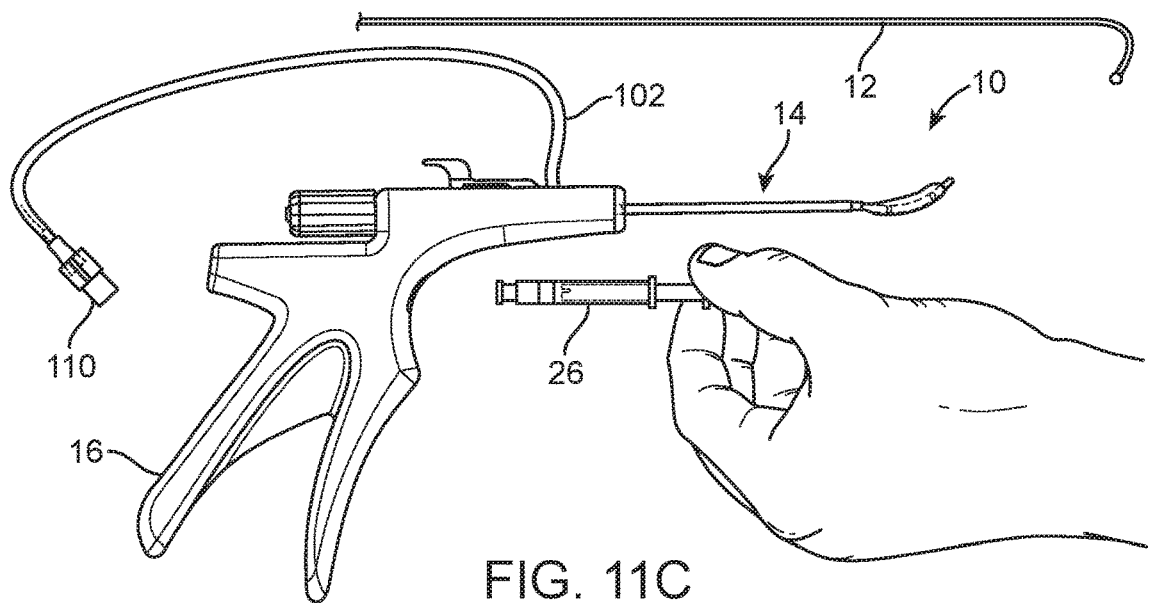
Figure 11D:
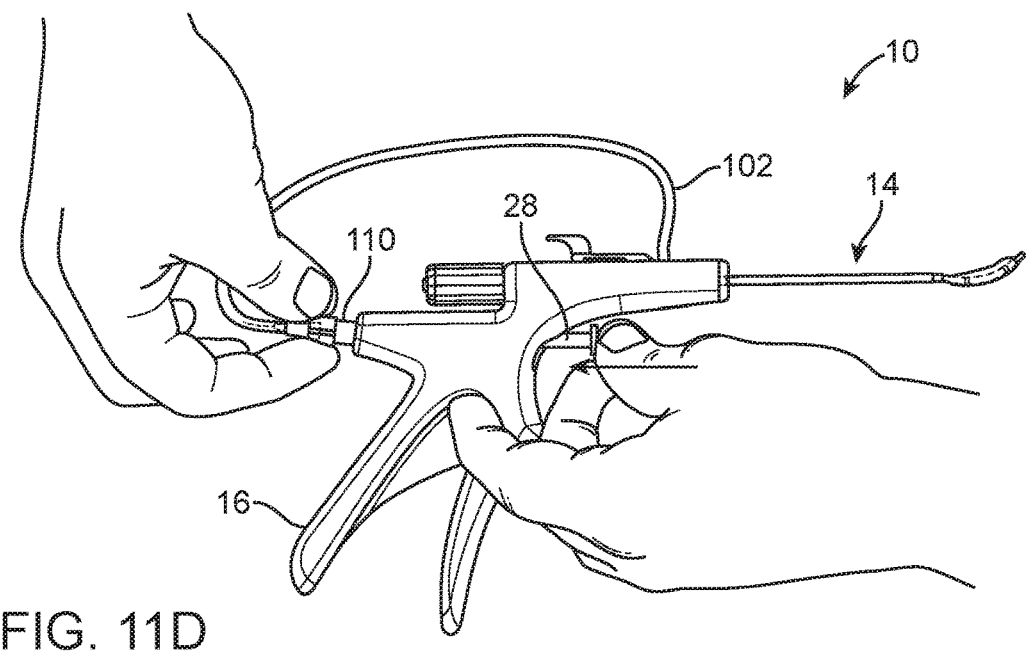
Figure 11E:
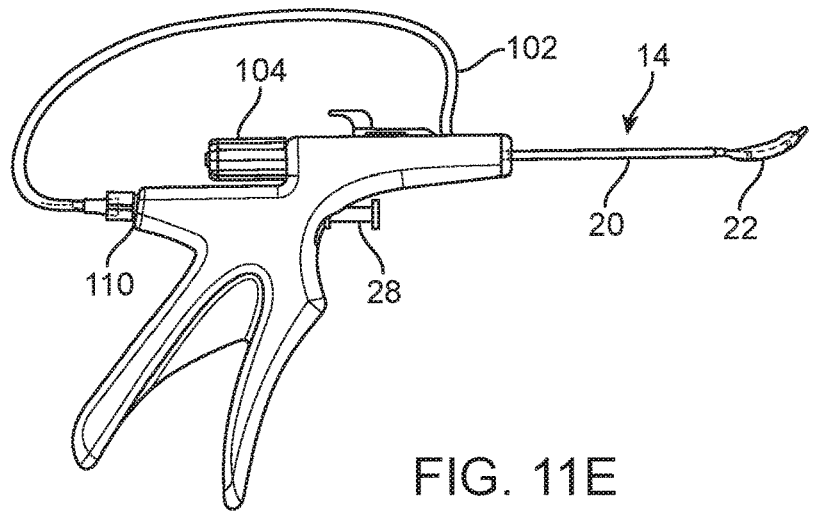
Figure 11F:
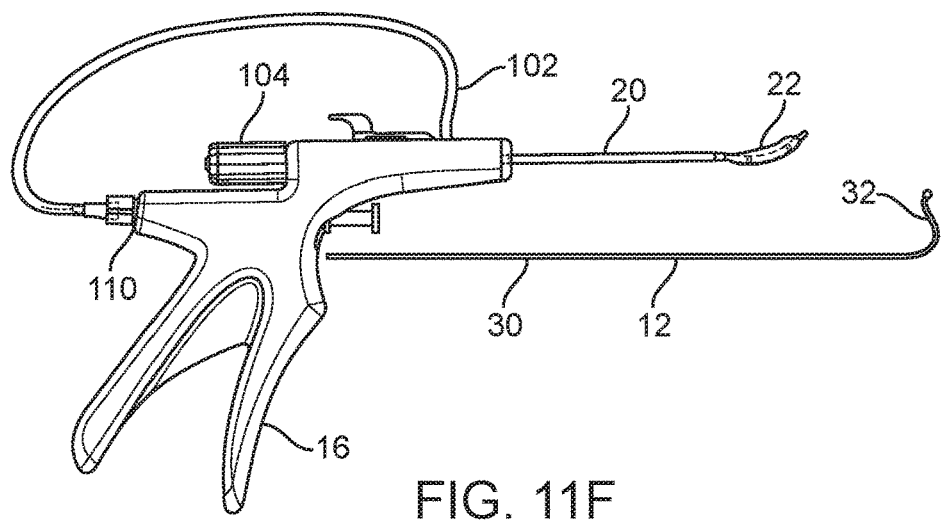

Referring to FIGS. 11C-11E, in some embodiments, the next preparation steps for seeker/dilator system 10 may be to insert inflation device 26 into an inflation device housing on handle 16 and connect proximal end connector 110 (such as a Luer connector) of inflation tube 102 with the distal end of inflation device 26. As illustrated in this embodiment, inflation device 26 may in some embodiments be a syringe, which may be an off-the-shelf syringe or a custom syringe made specifically for seeker/dilator system 10. FIG. 11C shows handle 16 and inflation device 26 before they are attached. FIG. 11D shows the two components being attached and proximal end connector 110 being attached to the distal end of inflation device 26. Before attaching the proximal end connector to inflation device 26, the user may engage in one or more optional steps to help ensure proper inflation of the balloon. For example, in one embodiment, a separate syringe may be used to empty any residual air from dilation member 34 ("balloon," in this embodiment) and fill dilation member 34 with inflation fluid, such as saline. Proximal end connector 110 may then be attached to the distal end of inflation device 26, and balloon 34 is then ready to inflate. FIG. 11E shows system 10 after these steps have been performed.

Figure 11G:
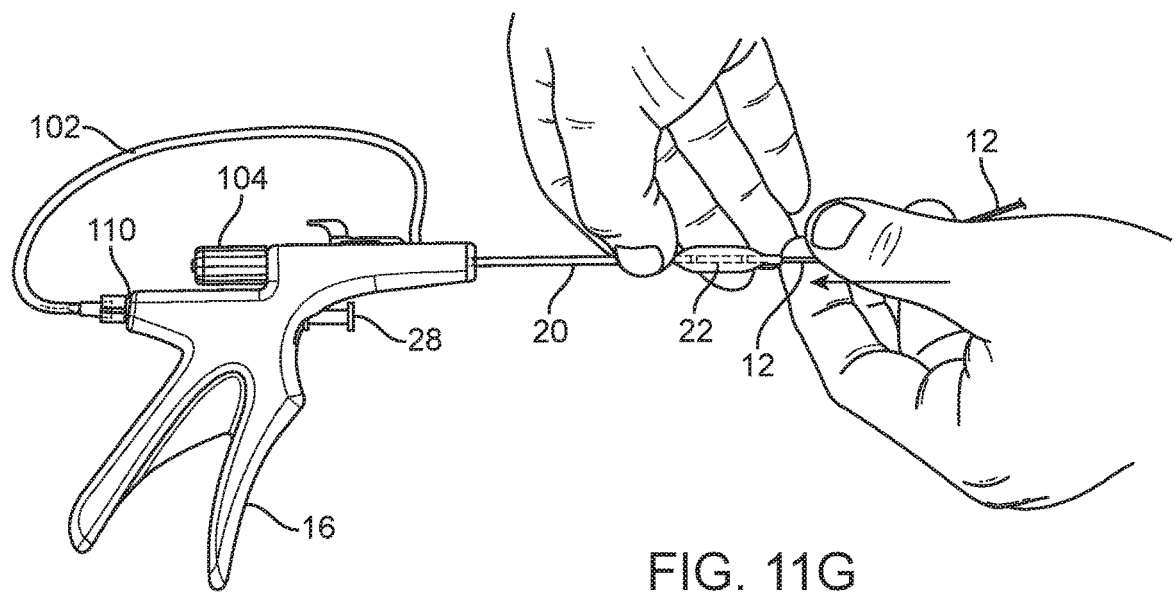
Figure 11H:
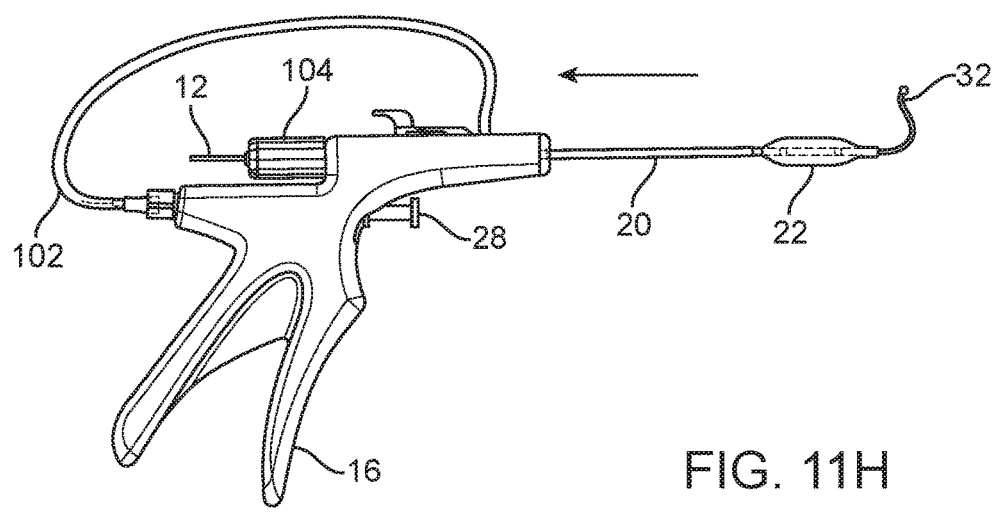
Figure 11I:
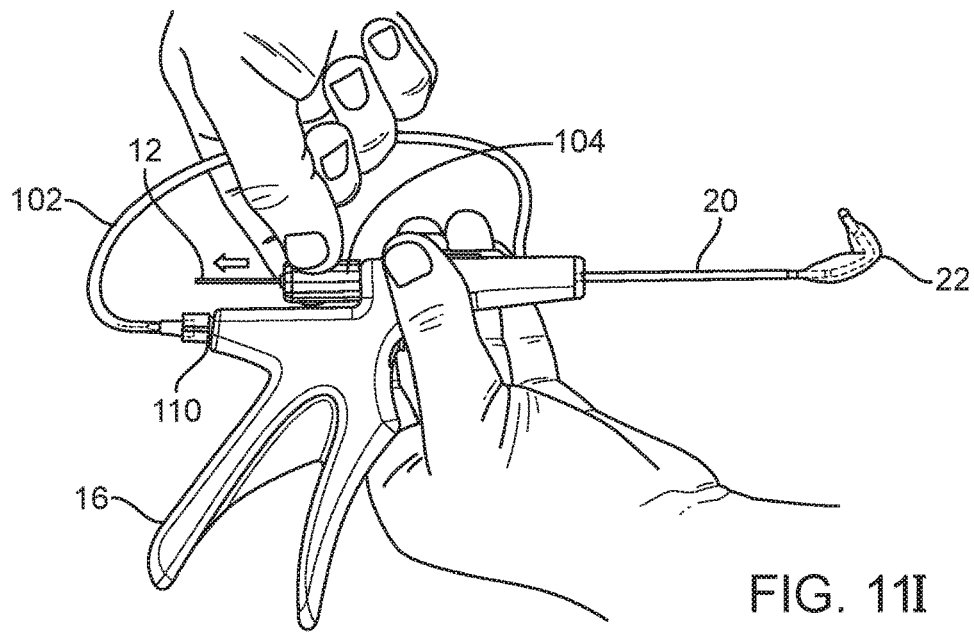

Next, with reference to FIGS. 11F-11I, a proximal end of seeker 12 (which may also be referred to as a "stylet," "finder" or other similar name) is advanced into a distal end of dilator device 14, through a seeker lumen (or "inner lumen," not visible in the figures). As described extensively above, seeker 12 includes elastic distal portion 32, which has a specific default shape designed to facilitate accessing a given anatomical structure or location. As illustrated in FIG. 11G, seeker 12 is threaded through elastic distal portion 22 and rigid proximal shaft 20 of dilator device 14 and then through handle 16, until the proximal end of seeker 12 passes through and protrudes out of seeker locking mechanism 104. FIG. 11H shows seeker 12 advanced into dilator 14 far enough that only elastic distal portion 32 protrudes out of the distal end of dilator 14. Seeker 12 is then typically advanced farther proximally, to a position as shown in FIG. 11I, where only ball-shaped tip 18 of seeker 12 protrudes out of the distal end of dilator 14, and flexible distal portion 22 of dilator 14 at least partially assumes the default shape of elastic distal portion 32. At this point, seeker locking mechanism 104 may be turned to lock the proximal portion of seeker 12 to handle 16. Handle 16, dilator 14 and seeker 12 are thus all locked together. Inflation device 26 is also attached to handle 16, and thus seeker/dilator system 10 is ready for operation.

As mentioned above, in some embodiments, a balloon dilation device may include a pressure release valve, such as in the plunger of an inflation portion of the device, in a connector hub of the device and/or the like. The purpose of a pressure release valve is to release excess inflation pressure imposed on the balloon of the dilation device. If too much inflation pressure is applied to the balloon, it may cause balloon rupture or unwanted damage to tissues. Although pressure release valves are one solution to over-inflation, other embodiments are also possible.

Referring now to FIGS. 12A-12E, an alternative embodiment of an inflation pressure management device is illustrated. In this embodiment, an inflation plunger 128 may include a pressure indicator (or "excess pressure indicator"), which may be a mechanical, electrical or electromechanical indicator, for example. The indicator alerts a user when an excess amount of inflation pressure is applied to the dilator device (such as a barrel of a syringe and/or an inflatable balloon) by the user to plunger 128. In this description, the phrases "excess pressure" and "excess force" may sometimes be used interchangeably, since excess force applied by the user to plunger 128 may sometimes result in excess inflation pressure applied by plunger 128 to the inflation member.

In the embodiment of FIGS. 12A-12E, plunger 128 is designed with a mechanical excess pressure indicator. In this embodiment, plunger 128 includes a shaft 130 with an inner cavity 133, a proximal wide base 140, and a distal solid portion 131. A spring 134 is disposed inside cavity 133 of shaft 130, and a rod 136, with a T-shaped distal end 138, extends through the inside of spring 134. A cap 132 with a hole 144 in it is disposed at the proximal-most end of plunger 128. The proximal end of rod 136 extends into hole 144. Spring 134 is located within cavity 133, between a distal end of cap 132 and T-shaped distal end 138 of rod 136. Cap 132 has a narrow distal portion that fits into, and is free to move back and forth in, the proximal end of cavity 133. Cap 132 and wide base 140 of shaft 130 are coupled to a proximal housing 142 of plunger 128, in this embodiment. Cap 132 is fixedly attached to housing 142, such that cap 132 and housing 142 slide together, proximally and distally, relative to wide base 140 of shaft 130. As cap 132 is depressed, typically by a thumb (or sometimes another finger) of a user, cap 132 and housing 142 may slide down over rod 136, thus causing rod 136 to protrude through hole 144 and poke into the user's thumb, thus providing tactile feedback. This is described in greater detail immediately below.

Figure 12A:
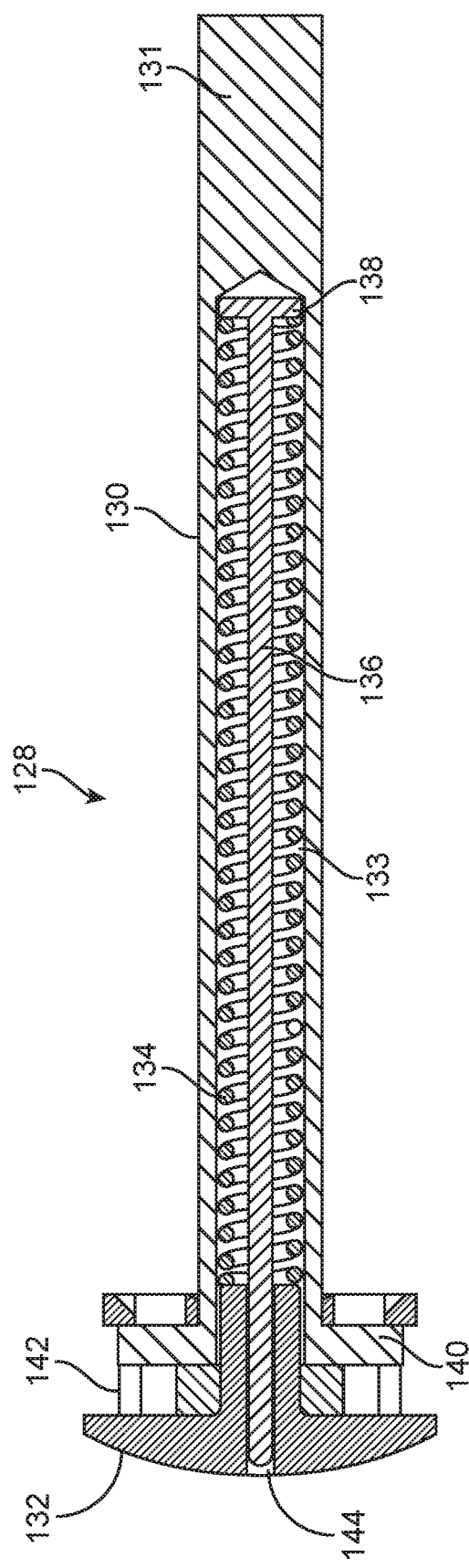
FIG. 12A is a side, cross-sectional view of an inflation plunger with a pressure indicator, for use in a dilation device, according to one embodiment.
Figure 12B:
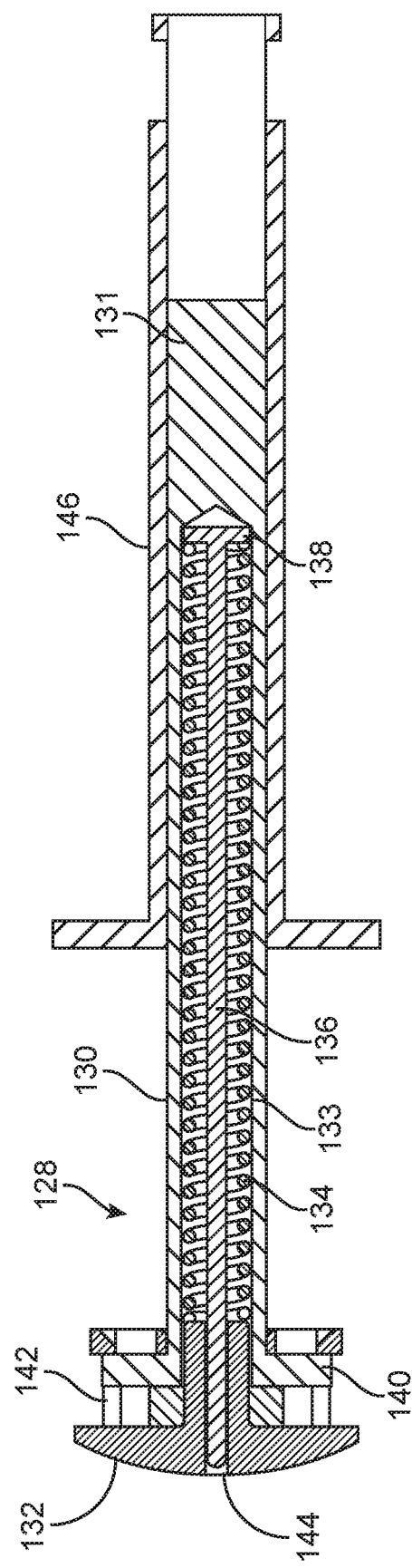
FIGS. 12B and 12C are side, cross-sectional views of the inflation plunger of FIG. 12A, illustrated with a syringe barrel, illustrating operation of the plunger.
Figure 12C:
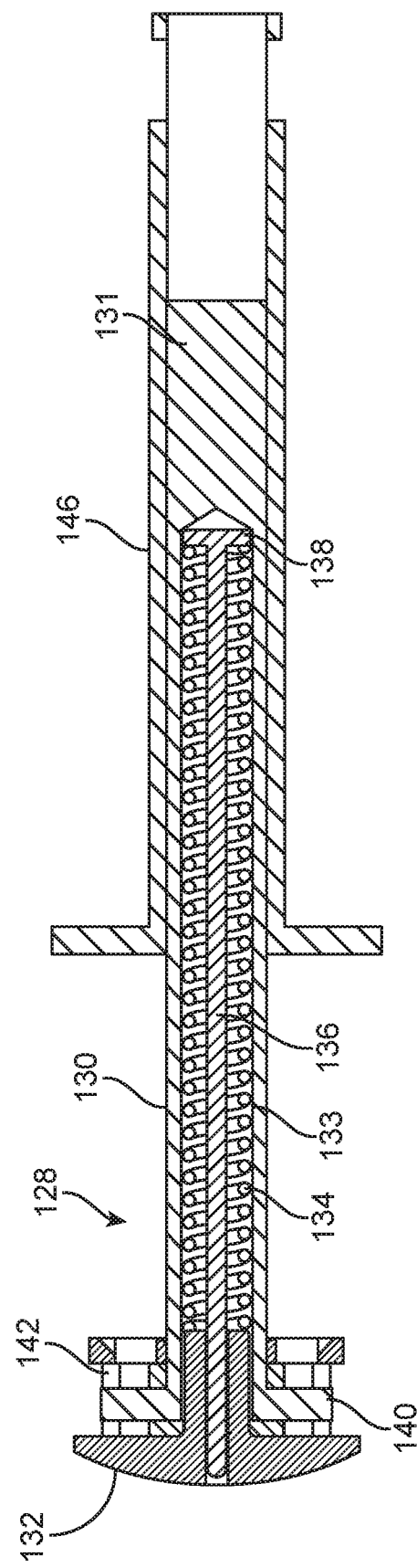

FIGS. 12B and 12C illustrate the operation of plunger 128. In these figures, plunger 128 is shown partially inserted into a syringe barrel 146. This combination of plunger 128 and barrel 146 may be used in some embodiments of a dilation device, such as device 10, illustrated in FIGS. 11A-11I. In alternative embodiments, however, plunger 128 may be used by itself in a handle of a balloon dilation device, or as part of another type of inflation device. Thus, syringe barrel 146 is shown here for illustrative purposes only.

As shown in FIG. 12B, as a physician or other user depresses plunger 128 by pressing down on cap 132 (typically but not necessarily with a thumb), inflation fluid (not shown) exits the distal end of syringe barrel 146 to inflate the balloon or other inflation member (also not shown). As long as an appropriate (or "desired" or "preset") amount of inflation pressure is applied to the inflation member by the user, plunger 128 will remain in a configuration like that shown in FIG. 12B, spring 134 will not compress further, and rod 136 will not protrude through hole 144. In other words, as long as the user exerts a force smaller than the force that spring 134 is pre-loaded with, then spring 134 will not compress, shaft 130 and cap 132 move together, further into syringe barrel 146, and the pressure inside syringe barrel 146 continues to increase. Once the force exerted by the user on cap 132 exceeds the pre-loaded force in spring 134, however, spring 134 starts to compress, cap 132 moves closer to wide base 140, and rod 136 protrudes out through hole 144.

The appropriate amount of pressure created inside syringe barrel 146 and the amount of force applied by the physician/user via cap 132 may vary from embodiment to embodiment, according to the required pressure inside syringe barrel 146. Thus, the geometrical dimensions and preloaded force in spring 134 may be adjusted, from embodiment to embodiment, to correlate and indicate to the user when such pressure is reached. The force/pressure required may depend on a number of different factors, such as but not limited to the diameters of barrel 146 and shaft 130, the type and/or size of inflation member in the dilation device and/or the like. In some embodiments, for example, it may be desired to inflate a balloon of the dilation device to approximately 10 atmospheres (ATM) of pressure. If shaft 130 is approximately 5 mm in diameter, it requires approximately 2 kg of force applied to cap 132 to reach 10 ATM of pressure. In some embodiments, for example, shaft 130 diameters may range from about 3 mm to about 7 mm, and the desired applied force may range from about 0.7 kg to about 4 kg. These are only examples, however, and should not be interpreted as limiting the scope of this embodiment of plunger 128 or any other embodiment.

Referring to FIG. 12C, if the user continues to depress plunger 128 past a certain, predetermined pressure within syringe barrel 146, spring 134 starts to compress, cap 132 and housing 142 move down over wide base 140 of shaft 130, and rod 136 protrudes through hole 144. The user will feel rod 136 protruding through cap 132 into his or her thumb or other finger used to depress cap 132. In this manner, plunger 128 provides instant tactile feedback to the user that excess inflation pressure has been reached inside syringe barrel 146. The user can then stop applying force or reduce the amount of force being applied, for example until rod 136 moves distally back into hole 144. In alternative embodiments, this tactile feedback may be accompanied by additional tactile feedback, visual feedback and/or audio feedback. For example, in one embodiment rod 136 may be an electrode or may be attached to an electrode, and plunger 128 may be configured to give the user a mild shock if excess force is applied. In another embodiment, instead of a shock, a sound alert and/or vibration may be used. Such additional or alternative feedback is not necessary, however, with the illustrated embodiment.

Figure 12D:
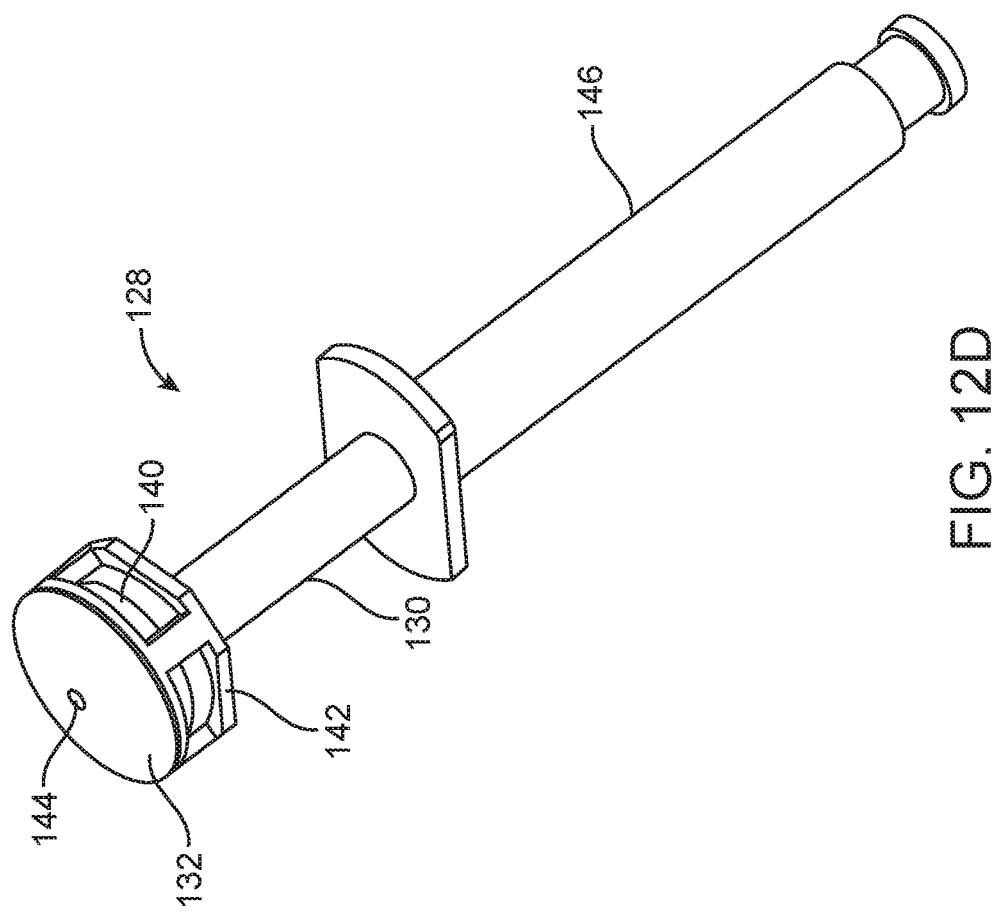
FIGS. 12D and 12E are perspective views of the inflation plunger and syringe barrel of FIGS. 12B and 12C.
Figure 12E:
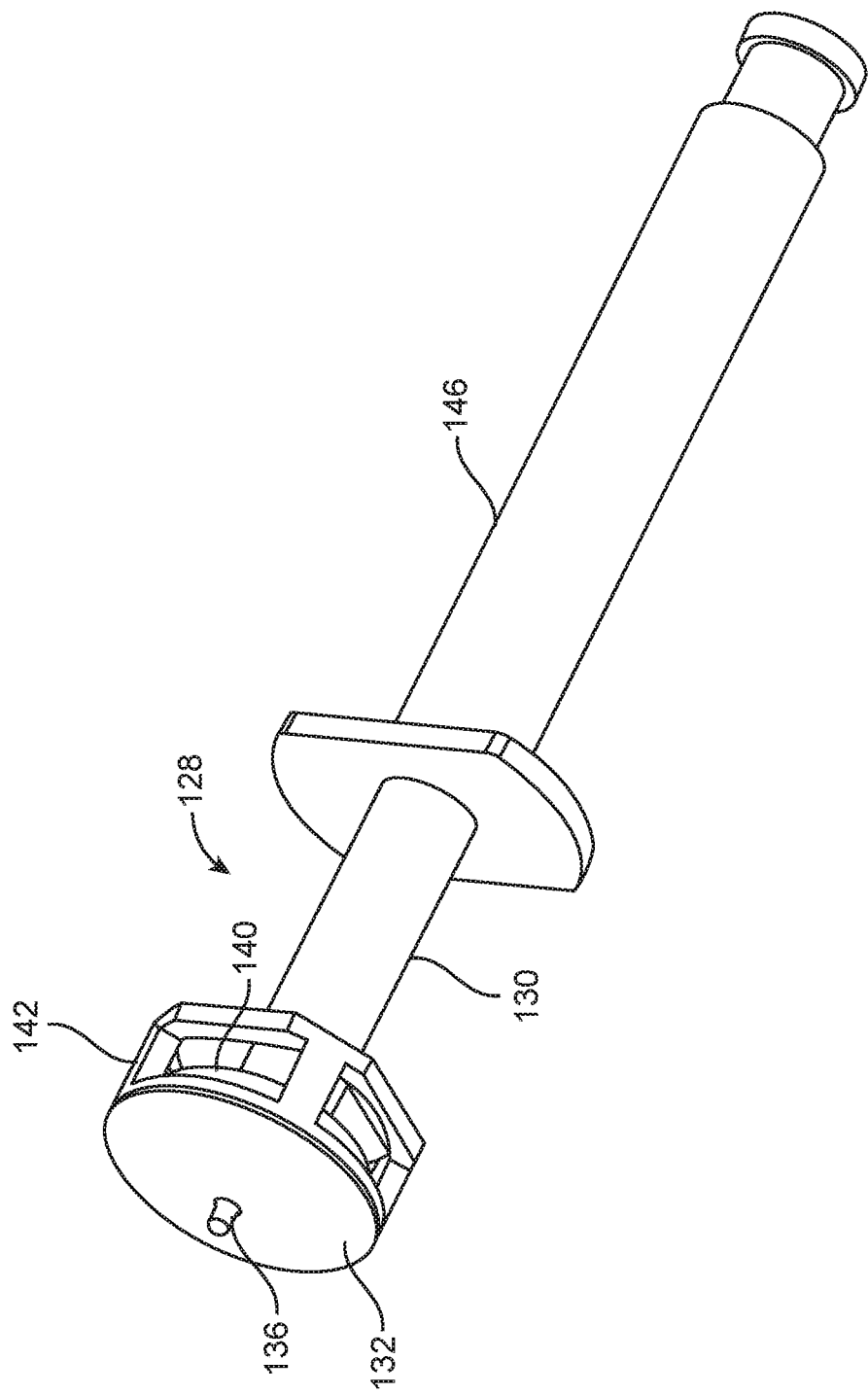

FIGS. 12D and 12E are perspective views of plunger 128 and syringe barrel 146, illustrating the two configurations just described—i.e., before excess force is applied (resulting in excess pressure) (FIG. 12D), and after excess pressure is applied (resulting in excess pressure) (FIG. 12E). These two figures more clearly illustrate the relationship of cap 132 and wide base 140 to housing 142, and they also illustrate how wide base 140 moves relative to cap 132 and housing 142.

Figure 13A:
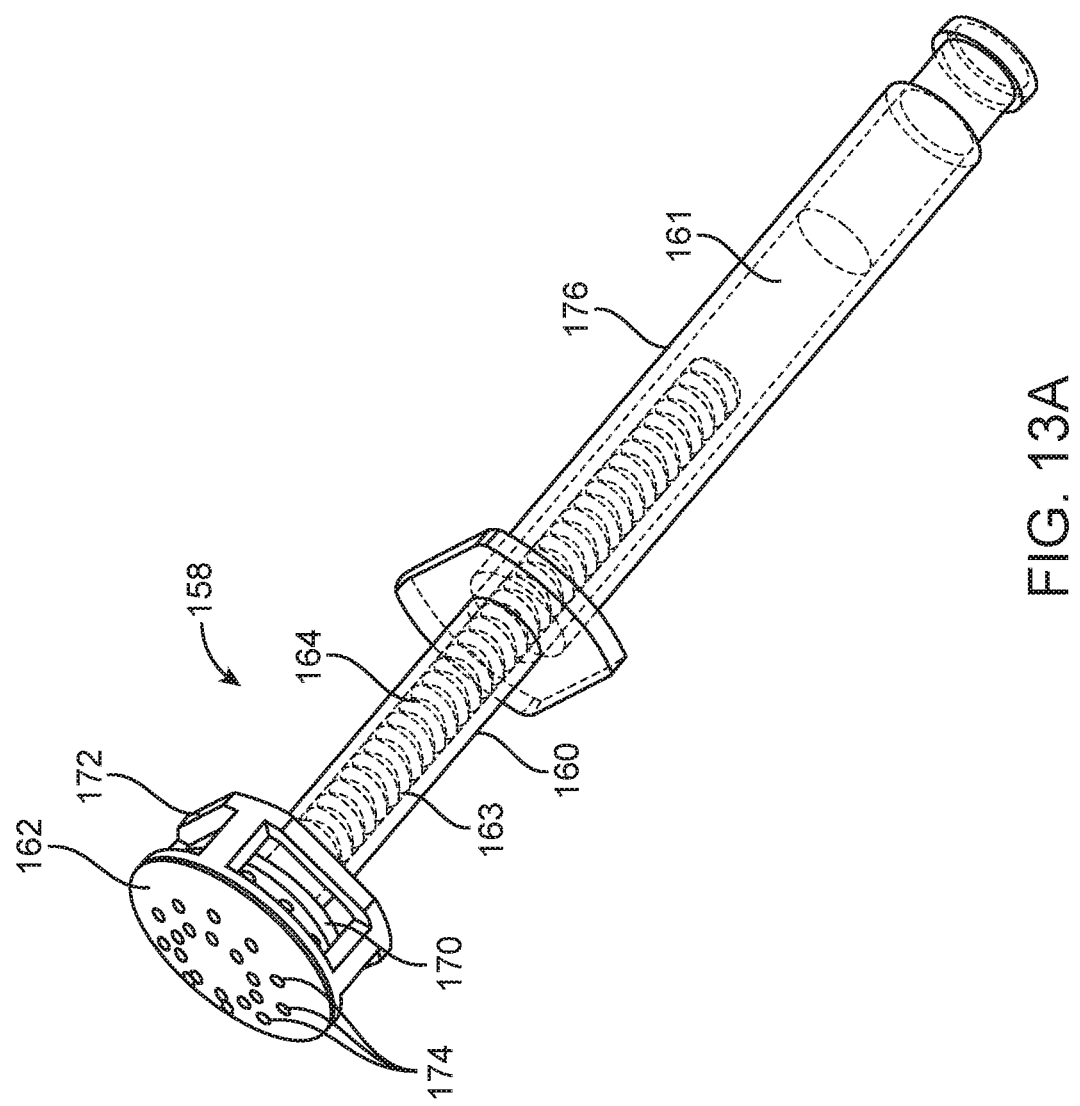
FIG. 13A is a perspective view of an inflation plunger and syringe barrel, portions of which are transparent in this view, according to an alternative embodiment.
Figure 13B:
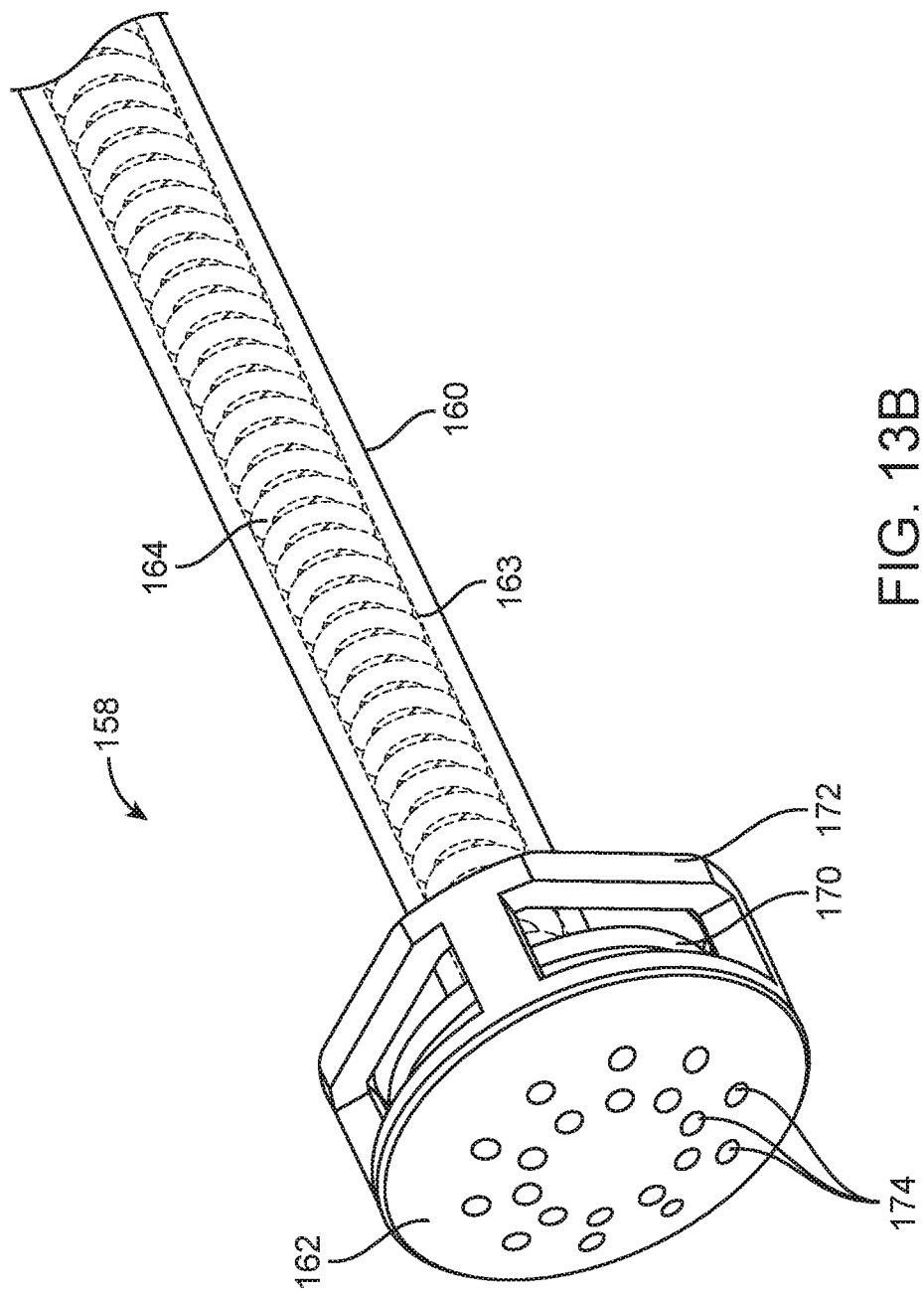
FIGS. 13B and 13C are perspective, partial cross-sectional views of a proximal portion of the plunger of FIG. 13A, illustrating operation of the plunger.
Figure 13C:
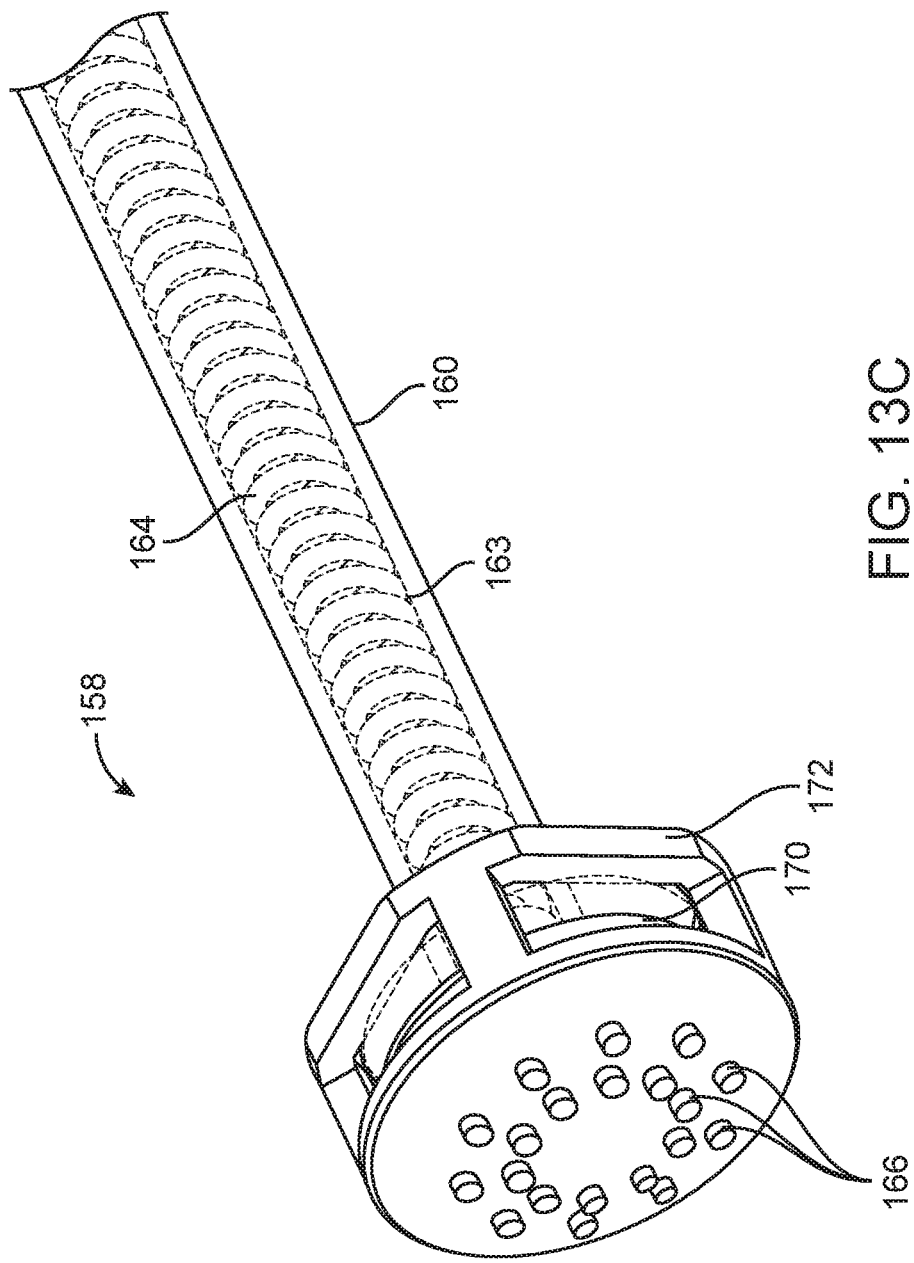
Figure 13D:
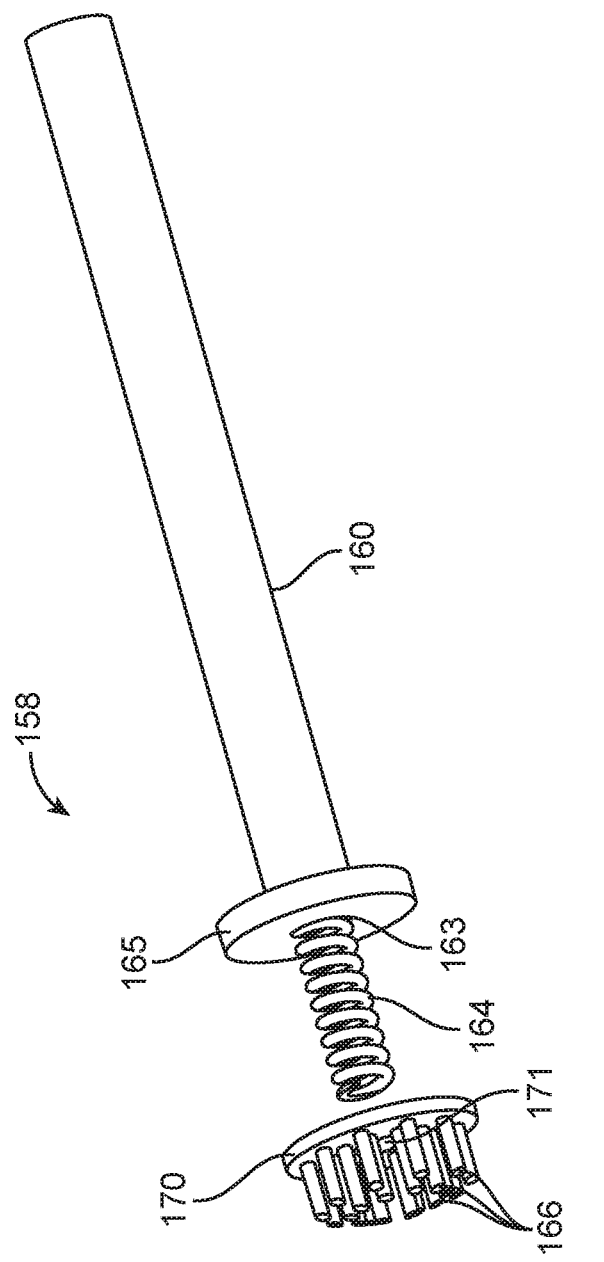
FIG. 13D is an exploded view of the inflation plunger of FIGS. 13A-13C.
Figure 13D:
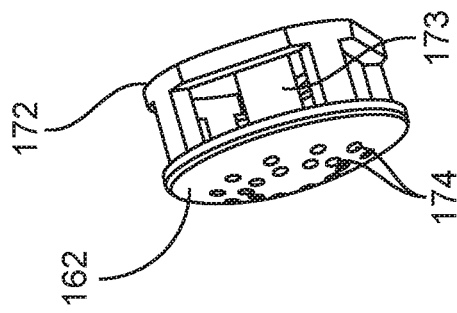

Referring now to FIGS. 13A-13D, an alternative embodiment of a plunger 158 with excess inflation force indicator is illustrated. FIG. 13A shows plunger 158 with a syringe barrel 176. As with the previous embodiment, plunger 158 is designed with a mechanical excess pressure indicator. FIGS. 13A and 13D illustrate the various parts of plunger 158 most clearly. In this embodiment, plunger 158 includes a shaft 160 with an inner cavity 163, a proximal wide base 165 (FIG. 13D), and a distal solid portion 161. A spring 164 is disposed inside cavity 163 of shaft 160. As illustrated in FIG. 13D, rather than using a rod, as in the previous embodiment, in this embodiment spring 164 extends through a hole 171 of a platform 170 and is attached to a tube 173 of a housing 172. (In one embodiment, platform 170 and wide base 165 may be one piece.) A cap 162 is attached to the proximal end of housing 172 and includes multiple apertures 174. Multiple pins 166 on platform 170 are sized and located to pass through apertures 174, and platform 170 is attached to wide base 165 of shaft 160. (In other embodiments, platform 170 may be eliminated, and pins 166 may be placed on wide base 165.) In this embodiment, platform 170 and pins 166 are fixed, relative to shaft 160, and cap 162 and housing 172 move proximally and distally, relative to platform 170 and pins 166, depending on the amount of force/pressure being applied.

FIGS. 13B and 13C illustrate operation of plunger 158. FIG. 13B shows plunger 158 in a configuration in which the force applied does not exceed the pre-loaded force in spring 164, so spring 164 has not compressed, and pins 166 are not protruding out of holes 174. FIG. 13C shows plunger 158 in a configuration where the applied force exceeds the pre-loaded force in spring 164, and pins 166 are protruding. Pins 166 provide a tactile feedback to the user that less pressure/force should be applied. In an alternative embodiment, the height of pins 166 may be adjustable, for example to adjust the amount of acceptable or desired inflation pressure. (Similarly, the height of rod 136, from the previously described embodiment, may be adjusted in some embodiments.) For example, one embodiment may include a dial, knob or similar adjustment device, either on plunger 158 or on a different part of the dilation device, which allows the user to dial in the height of pins 166 and thus adjust when plunger 158 will indicate that the designated pressure has been reached. This means that the amount of pressure for which an indication is given may be adjusted on the go, in some embodiments. In other alternative embodiments, pins 166 and platform 170, or rod 136 of the previous embodiment, may be replaced with any other suitable mechanism for providing tactile feedback.

Referring now to FIGS. 14A-14D, in one embodiment, an inflation system 200 for inflating a balloon dilation device as described herein may include an inflation device 202 and a holder 220. Inflation device 202 may include an inflation plunger, which may be the same as, or similar to, any of the plunger embodiments described above and/or may include any of the features described above. In this embodiment, the inflation plunger includes a housing 204, multiple rods 206, a shaft 208 and an inner spring within shaft 208 (not visible in FIGS. 14A-14D). Because various inflation plunger embodiments and features were described above, in relation to FIGS. 12-13, those details will not be repeated here. Inflation device 202, in this embodiment, further includes a syringe barrel 212 with a finger rest ledge 214 on its proximal end, and an outer, automatic deflation spring 210 disposed around shaft 208, between finger rest ledge 214 and housing 204.

Figure 14A:
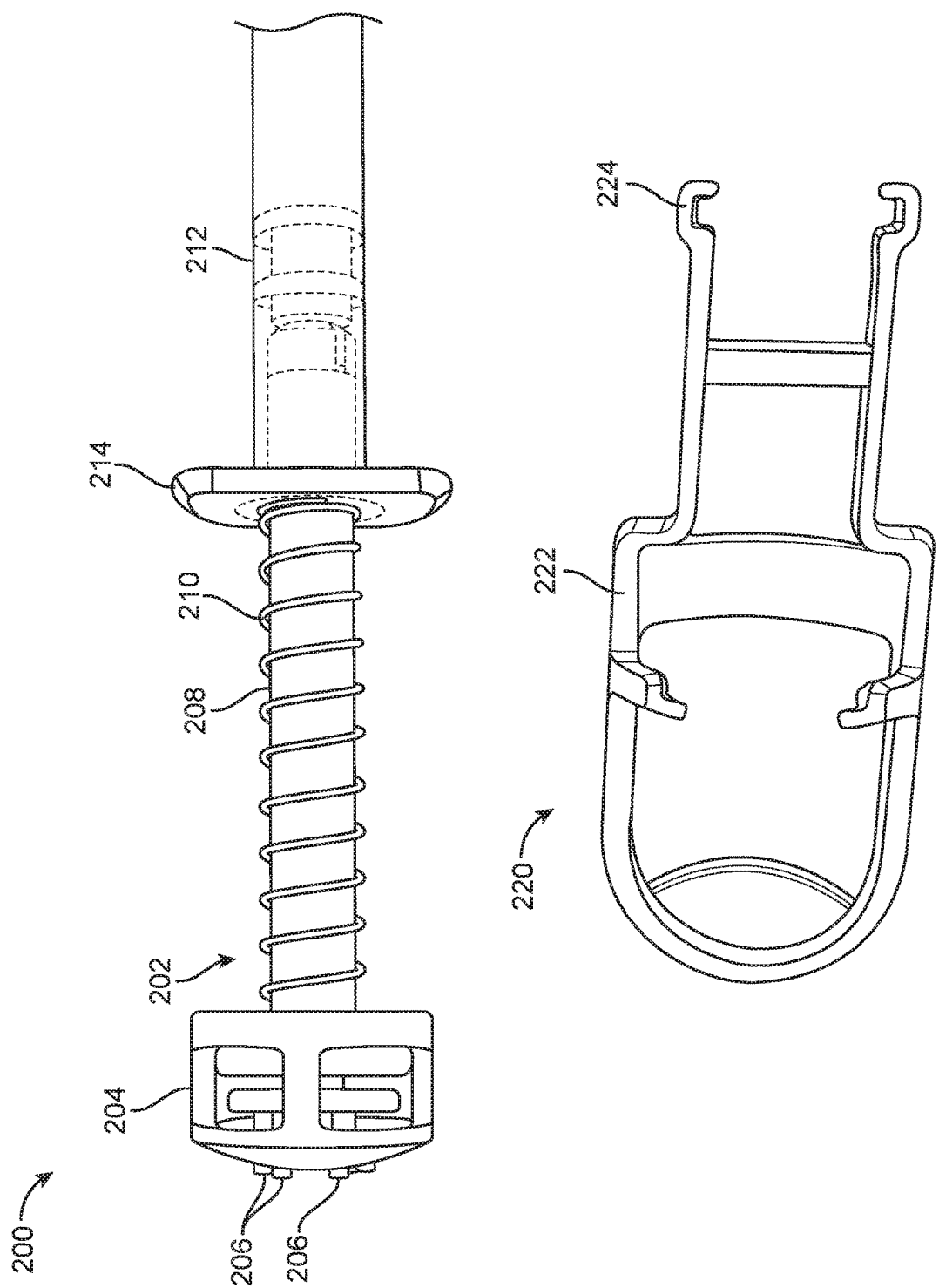
FIGS. 14A-14C are unassembled, perspective and side views, respectively, of an inflation device and a holder for same, according to one embodiment.
Figure 14B:
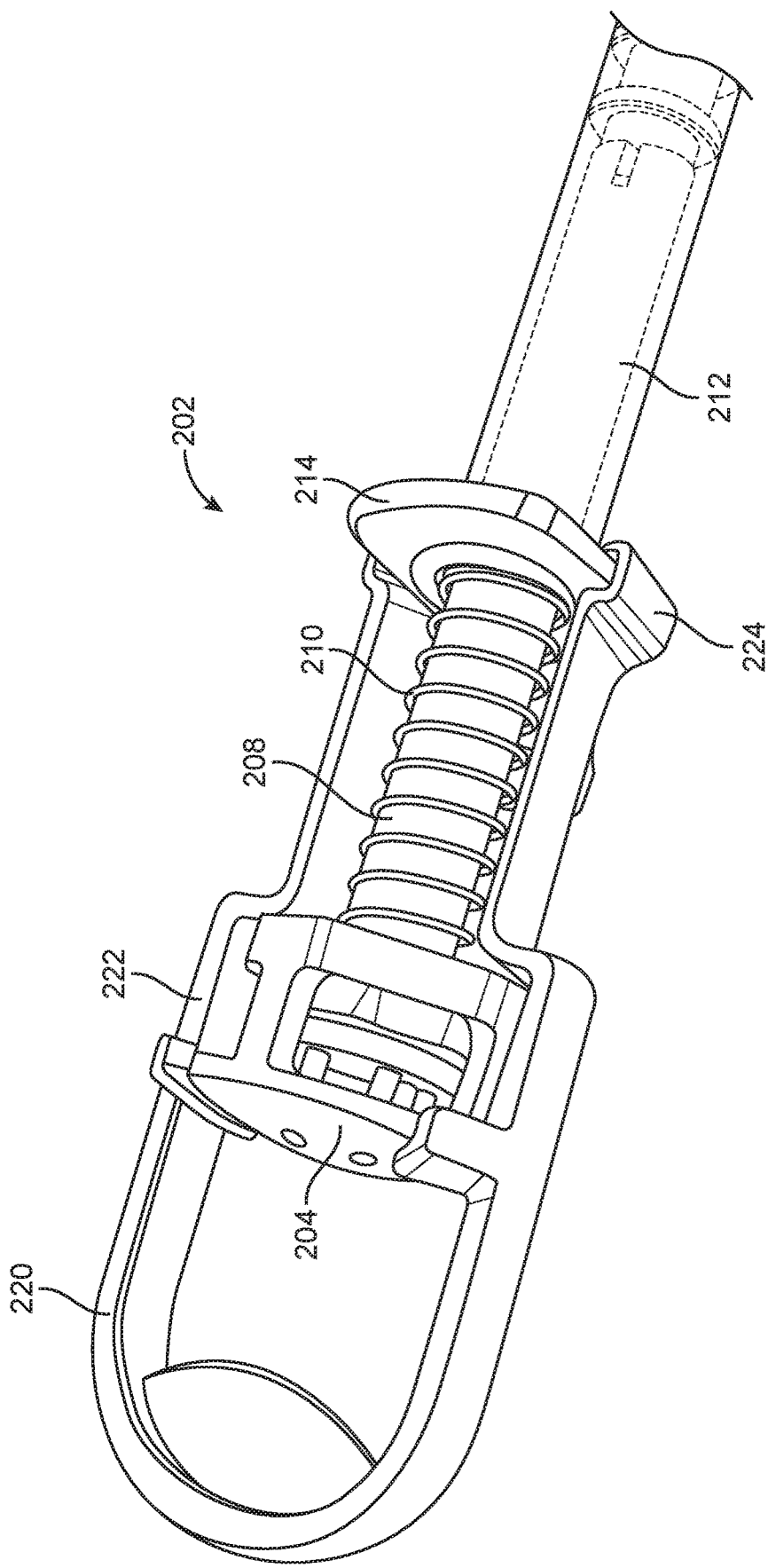
Figure 14C:
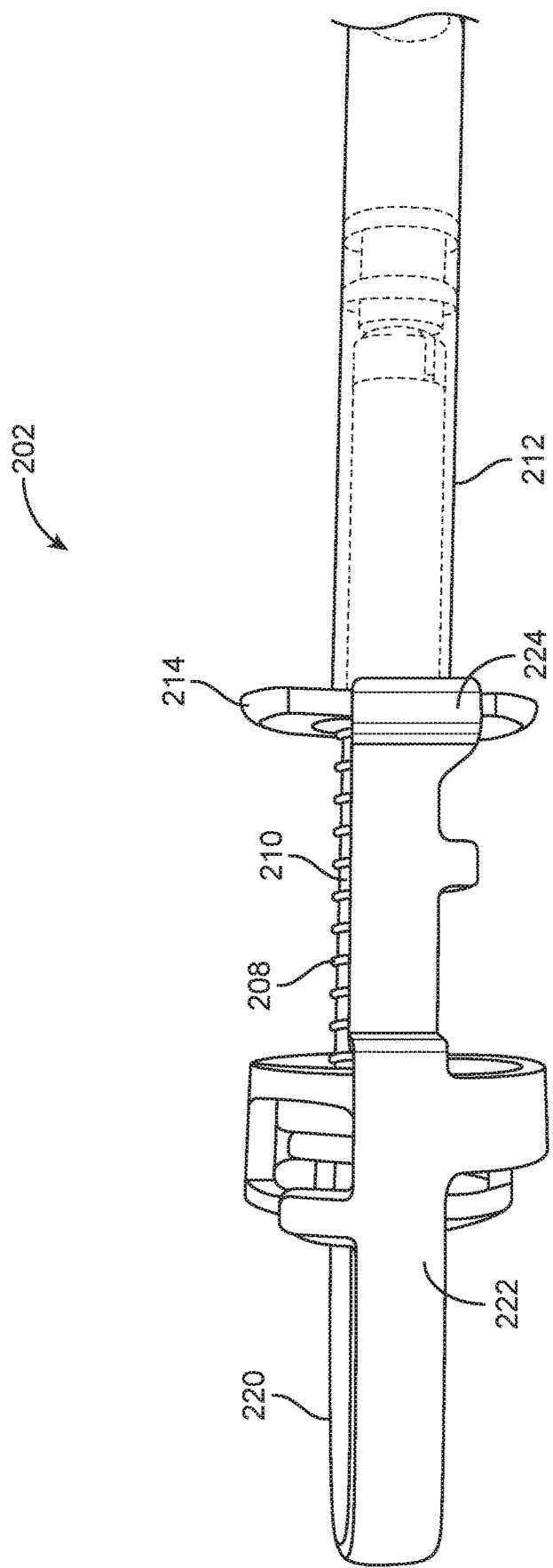
Figure 14D:
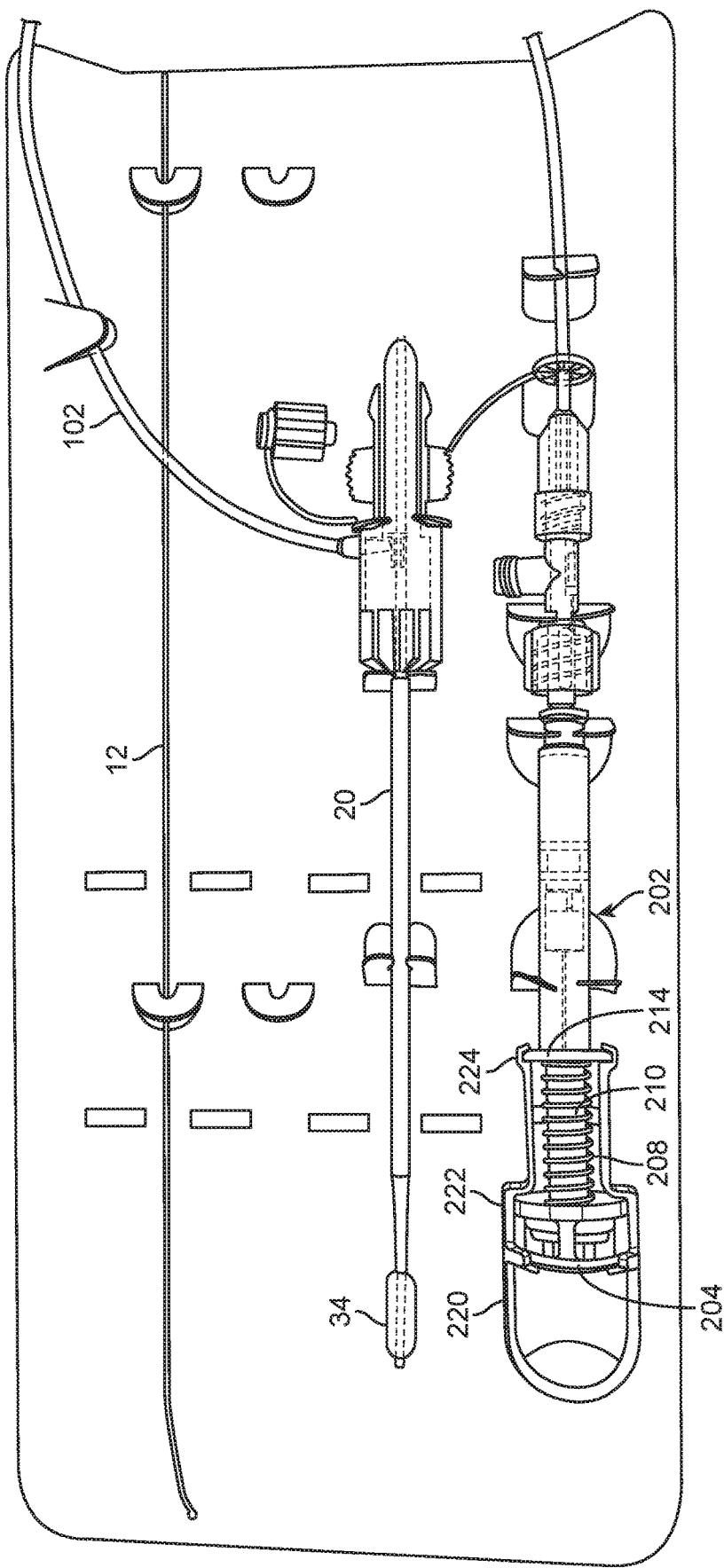
FIG. 14D is a top view of a sinus dilation kit, including the inflation device and holder of FIGS. 14A-14C, along with a seeker and balloon inflation device, according to one embodiment.

Holder 220 includes a top portion 222 for holding housing 204 and a bottom portion for holding finger rest ledge 214. Holder 220 acts to hold inflation device 202 in a desired position before use, so that shaft 208 is extended out of syringe barrel 212 by a desired distance. Holder 220 is shown detached from inflation device 202 in FIG. 14A, as would occur just before use of inflation device 202. FIG. 14B is a perspective view of inflation device 202 coupled with holder 220. To activate inflation device 202, the user would remove holder 220 by moving it laterally, relative to inflation device 202, to move housing 204 out of the open side of the top portion 222 of holder 220. FIG. 14C is a side view of holder 220 and inflation device 202, showing that holder 220 is asymmetrical and thus provides "directionality" when coupled with inflation device 202. This directionality helps the user advance the combined inflation device 202/holder 220 into the handle of the balloon inflation system (as in the assembly method described in FIGS. 11A-11I). FIG. 14D shows inflation device 202 and holder 220 combined in a kit, including the dilator device, with its shaft 20 and balloon 34, seeker 12 and inflation tube 102. Any of the components and parts of a balloon dilation system, as described above, may also be provided as part of the kit.

With continuing reference to FIGS. 14A-14D, in using a balloon dilation system as described herein, it is important to fill balloon 34 with the right amount of saline (or other inflation fluid in alternative embodiments). In the embodiment of FIGS. 14A-14D, this may be particularly important, since automatic deflation spring 210, when freed from constraint, pushes back the plunger to completely empty balloon 34. Some embodiments of the balloon dilation system may include a two-way luer lock, which connects with inflation tube 102 on one side and with the balloon inflation lumen on the opposite side. The luer lock includes a third connection, which may be covered with a cap when inflation device 202 is in regular use. During setup of the balloon dilation system, the user connects a regular syringe, filled with saline, to the third connection, then draws air from the system by pulling on the regular syringe until balloon 34 is completely deflated, while the syringe is pointing downward so that air will be drawn above saline level, and then presses the regular syringe to fill the system with saline. Once balloon 34 is completely filled, the syringe is disconnected from the third luer connection, and that connection is capped with the cap so that the system is airtight.

Holder 220 helps ensure that the balloon dilation system is filled with just enough saline so that when automatic deflation spring 210 is released it will empty balloon 34. To accomplish this, holder 220 holds housing 204 of inflation device 202 in place, pressed into syringe barrel 212 just enough while the dilation system is filled with saline so that automatic deflation spring 210 pushes the piston back enough to empty balloon 34 completely. Holder 220 also holds the piston in place so that it is not pulled in when air is pulled out of the system during setup and not pushed out while saline is filled into system 200, so that the amount of saline in system 200 is fixed and pre-determined. Holder 220 holds the piston pressed in enough so that automatic deflation spring 210 empties balloon 34 completely when released, and it also allows the piston enough room to be further pressed in, so that the inflation pressure inside balloon 34 can reach 10 atmospheres without the piston going all the way to the bottom of the syringe barrel 212. As mentioned above, holder 220 may be provided to the user in an assembled configuration, already attached to inflation device, as in FIGS. 14B-14D. Before starting the balloon dilation procedure, the user simply pushes holder 220 away, laterally, off of inflation device 202.

Although the above description is believed to be complete and accurate, the description is directed toward various exemplary embodiments, and these examples should not be interpreted as limiting the scope of the invention as it is defined by the claims. For example, various alternative embodiments of a dilation system described herein may include fewer components or a greater number of components than the embodiments described above. The methods described herein may also include fewer steps or a greater number of steps and/or the method steps may be performed in a different order. Therefore, the embodiments described herein should not be interpreted as limiting the scope of the invention.

We claim:

1. A system for dilating a paranasal sinus ostium in a patient, the system comprising:
   a seeker device having a proximal shaft and a distal portion, wherein the distal portion has a shape with at least one curve configured to facilitate advancement of a distal end of the distal portion into the paranasal sinus ostium;
   a dilator device, comprising:
      a proximal portion, comprising an inner lumen configured for passage of the seeker; and
      a flexible distal portion comprising a balloon, wherein the inner lumen extends through the balloon, and wherein the flexible distal portion is sufficiently flexible to assume the shape of the distal portion of the seeker device when the flexible distal portion is located over the distal portion of the seeker device;
   a handle attached to the proximal shaft of the seeker device and the proximal portion of the dilator device;
   an inflation device attached to the handle, wherein the inflation device comprises:
      a syringe with a barrel and a plunger with an excess pressure indicator; and
      an automatic deflation spring coupled with the plunger to cause the dilation member to automatically deflate if the plunger is released from constraint,
      wherein the inflation device is configured to allow a user to hold the handle with one hand and advance the inflation substance out of the inflation device to inflate the balloon with the same hand; and
   a holder removably attached to the inflation device to hold the plunger in a stable position relative to the barrel of the syringe, to avoid unwanted deflation of the dilation member.

2. The system of claim 1, wherein the seeker device further comprises an atraumatic tip on the distal end of the distal portion.

3. The system of claim 1, wherein the seeker device is made of at least one material selected from the group consisting of stainless steel, titanium, Nitinol, other metals, PEEK, a copper-aluminum-nickel alloy, a shape-memory polymer, spring stainless steel, an elastic polymer, other shape-memory materials and other super-elastic materials.

4. The system of claim 1, wherein the at least one curve of the distal portion of the seeker device comprises:
   a first curve in a first plane; and
   a second curve in a second plane.

5. The system of claim 1, wherein the proximal portion of the dilator device comprises a rigid shaft permanently attached to the handle, wherein the proximal shaft of the seeker device is configured to pass through the inner lumen of the proximal portion of the dilator device and into the handle, and wherein the handle includes a locking mechanism for removably locking the proximal shaft of the seeker device to the handle.

6. The system of claim 1, wherein the proximal portion of the dilator device further includes an inflation lumen, and wherein the inner lumen of the dilator device is located coaxially within the inflation lumen.

7. The system of claim 1, wherein the proximal portion of the dilator device further includes an inflation lumen, and wherein the inner lumen of the dilator device is located beside the inflation lumen.

8. The system of claim 1, wherein the handle comprises a locking member configured to removably lock the proximal shaft of the seeker device to the handle, to prohibit the proximal shaft from moving relative to the handle or the dilator device.

9. The system of claim 8, wherein the proximal portion of the dilator device is permanently and fixedly attached to the handle.

10. The system of claim 8, wherein the proximal portion of the dilator device is removably attached to the handle.

11. The system of claim 1, wherein the inflation device further comprises a pressure release valve to prevent over-inflation of the dilation member.

12. The system of claim 1, further comprising a tube configured to connect a distal end of the syringe to the dilator device.

13. The system of claim 1, further comprising multiple alternative seeker devices, wherein the at least one curve of the distal portion of each of the seeker device and the multiple alternative seeker devices has a specific shape configured to facilitate access to one specific desired location, and wherein the one specific desired location is selected from the group consisting of a left maxillary sinus, a right maxillary sinus, a left frontal sinus, a right frontal sinus, a left sphenoid sinus, a right sphenoid sinus and a Eustachian tube.

14. The system of claim 1, wherein the plunger comprises a shaft with an inner cavity, and wherein the excess pressure indicator comprises:
   a cap on a proximal end of the plunger and having a hole;
   a spring disposed within the inner cavity and contacting the cap; and
   a rod in the inner cavity, within the spring and extending into the hole in the cap,
   wherein, when excess pressure builds up in the barrel of the syringe, the spring compresses and the rod extends through the hole in the cap to contact a user's thumb or other finger used to depress the plunger.

15. The system of claim 1, wherein the plunger comprises a shaft with an inner cavity, and wherein the excess pressure indicator comprises:
   a cap on a proximal end of the plunger and having multiple apertures;
   a spring disposed within the inner cavity;
   a platform attached to a proximal end of the spring; and
   multiple pins attached to the platform and extending into the multiple apertures in the cap,
   wherein, when excess pressure builds up in the barrel of the syringe, the spring compresses and the multiple pins extend through the multiple apertures in the cap to contact a user's thumb or other finger used to depress the plunger.

16. A system for dilating a paranasal sinus ostium in a patient, the system comprising:
   a seeker device having a proximal shaft and a distal portion, wherein the distal portion has a shape with at least one curve configured to facilitate advancement of a distal end of the distal portion into the paranasal sinus ostium;

a dilator device, comprising:
- a proximal portion, comprising an inner lumen configured for passage of the seeker; and
- a flexible distal portion comprising a balloon, wherein the inner lumen extends through the balloon, and wherein the flexible distal portion is sufficiently flexible to assume the shape of the distal portion of the seeker device when the flexible distal portion is located over the distal portion of the seeker device;

a handle attached to the proximal shaft of the seeker device and the proximal portion of the dilator device; and an inflation device attached to the handle, wherein the inflation device comprises a syringe with a plunger with an excess pressure indicator, wherein the inflation device is configured to allow a user to hold the handle with one hand and advance the inflation substance out of the inflation device to inflate the balloon with the same hand, wherein the plunger comprises a shaft with an inner cavity, and wherein the excess pressure indicator comprises:
- a cap on a proximal end of the plunger and having a hole;
- a spring disposed within the inner cavity and contacting the cap; and
- a rod in the inner cavity, within the spring and extending into the hole in the cap,
- wherein, when excess pressure builds up in the barrel of the syringe, the spring compresses and the rod extends through the hole in the cap to contact a user's thumb or other finger used to depress the plunger.

17. A system for dilating a paranasal sinus ostium in a patient, the system comprising:

a seeker device having a proximal shaft and a distal portion, wherein the distal portion has a shape with at least one curve configured to facilitate advancement of a distal end of the distal portion into the paranasal sinus ostium;

a dilator device, comprising:
- a proximal portion, comprising an inner lumen configured for passage of the seeker; and
- a flexible distal portion comprising a balloon, wherein the inner lumen extends through the balloon, and wherein the flexible distal portion is sufficiently flexible to assume the shape of the distal portion of the seeker device when the flexible distal portion is located over the distal portion of the seeker device;

a handle attached to the proximal shaft of the seeker device and the proximal portion of the dilator device; and an inflation device attached to the handle, wherein the inflation device comprises a syringe with a plunger with an excess pressure indicator, wherein the inflation device is configured to allow a user to hold the handle with one hand and advance the inflation substance out of the inflation device to inflate the balloon with the same hand, wherein the plunger comprises a shaft with an inner cavity, and wherein the excess pressure indicator comprises:
- a cap on a proximal end of the plunger and having multiple apertures;
- a spring disposed within the inner cavity;
- a platform attached to a proximal end of the spring; and
- multiple pins attached to the platform and extending into the multiple apertures in the cap,
- wherein, when excess pressure builds up in the barrel of the syringe, the spring compresses and the multiple pins extend through the multiple apertures in the cap to contact a user's thumb or other finger used to depress the plunger.

* * * * *